(12) United States Patent
LV et al.

(10) Patent No.: US 9,604,935 B2
(45) Date of Patent: Mar. 28, 2017

(54) DEUTERATED PHENYL AMINO PYRIMIDINE COMPOUND AND PHARMACEUTICAL COMPOSITION CONTAINING THE SAME

(71) Applicant: Suzhou Zelgen Biopharmaceuticals Co., Ltd., Jiangsu (CN)

(72) Inventors: Binhua LV, Jiangsu (CN); Zelin Sheng, Jiangsu (CN); Benwen Cao, Jiangsu (CN)

(73) Assignee: Suzhou Zelgen Biopharmaceuticals Co., Ltd., Kunshan, Jiangsu (CN)

( * ) Notice: Subject to any disclaimer, the term of this patent is extended or adjusted under 35 U.S.C. 154(b) by 0 days.

(21) Appl. No.: 14/764,016

(22) PCT Filed: Jan. 28, 2014

(86) PCT No.: PCT/CN2014/071710
§ 371 (c)(1),
(2) Date: Oct. 30, 2015

(87) PCT Pub. No.: WO2014/114274
PCT Pub. Date: Jul. 31, 2014

(65) Prior Publication Data
US 2016/0060227 A1 Mar. 3, 2016

(30) Foreign Application Priority Data
Jan. 28, 2013 (CN) .......................... 2013 1 0032097

(51) Int. Cl.
| | | |
|---|---|---|
| *A61K 31/5377* | (2006.01) | |
| *C07D 239/42* | (2006.01) | |
| *C07D 413/12* | (2006.01) | |
| *A61K 45/06* | (2006.01) | |
| *C07B 59/00* | (2006.01) | |

(52) U.S. Cl.
CPC ........ *C07D 239/42* (2013.01); *A61K 31/5377* (2013.01); *A61K 45/06* (2013.01); *C07B 59/002* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 2011/0212077 A1 | 9/2011 | Noronha et al. | |
| 2015/0361051 A1* | 12/2015 | Silverman ............ | C07D 239/42 514/235.8 |

FOREIGN PATENT DOCUMENTS

| | | |
|---|---|---|
| WO | 2008109943 A1 | 9/2008 |
| WO | 2009029998 A1 | 3/2009 |
| WO | 2010151710 A2 | 12/2010 |
| WO | 2012071612 A1 | 6/2012 |

OTHER PUBLICATIONS

International Search Report issued Mar. 27, 2014 in International Application No. PCT/CN2014/071710.

\* cited by examiner

*Primary Examiner* — Samantha Shterengarts
(74) *Attorney, Agent, or Firm* — Panitch Schwarze Belisario & Nadel LLP

(57) ABSTRACT

The present invention relates to a deuterated phenyl amino pyrimidine compound and pharmaceutical composition containing the same. Specifically provided are a deuterated phenyl amino pyrimidine compound as represented by formula (I), and pharmaceutical composition containing the compound, or polymorph, pharmaceutically acceptable salt, hydrate or solvate thereof. The compound of the present invention can treat and/or prevent JAK kinase-related diseases, such as bone marrow proliferative disease, cancer, immunologic diseases and the like.

11 Claims, 1 Drawing Sheet

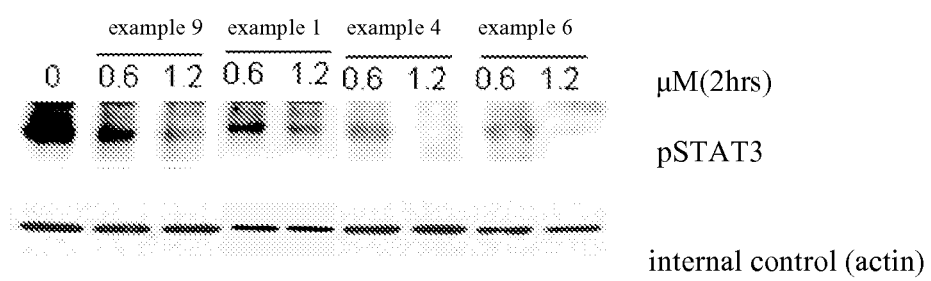

DEUTERATED PHENYL AMINO PYRIMIDINE COMPOUND AND PHARMACEUTICAL COMPOSITION CONTAINING THE SAME

CROSS-REFERENCE TO RELATED APPLICATION

This application is a Section 371 of International Application No. PCT/CN2014/071710, filed Jan. 28, 2014, which was published in the Chinese language on Jul. 31, 2014, under International Publication No. WO 2014/114274 A1, and the disclosure of which is incorporated herein by reference

TECHNICAL FIELD

The present invention relates to the field of pharmaceutical. Specifically, the present invention relates to a new deuterated phenylamino pyrimidine compound, or the pharmaceutical compositions which comprises said compound.

BACKGROUND OF THE INVENTION

JAK (Janus kinase) is a type of non-receptor tyrosine kinase family, in which there are 4 members found, which are JAK1, JAK2, JAK3 and TYK1, respectively. They do not comprise SH2 or SH3 in their structure, and there are two connected kinase areas in their C-terminal. The substrate of JAK is STAT, i.e., signaling transducers and activators of transcription. STAT is dimerizeted after being phosphorylated by JAK, and passes through nuclear membrane into nucleus to regulate the expression of relevant genes, which signal pathway is called JAK-STAT pathway, and plays a role in communication of hematopoietic cells and immune cells. Effective and specific inhibitors of the four JAK kinases currently known can be used to treat cancer, inflammation and other diseases. The selective JAK3 inhibitor, tofacitinib (product name: Xeljanz), of Pfizer is approved to be used for treating rheumatoid arthritis by the U.S. Food and Drug Administration in December of 2012.

Phenyl amino pyrimidine compounds and derivatives are a type of inhibitors of non-receptor tyrosine kinases such as JAK kinases. WO2008109943 and US2011212077 disclosed a series of phenyl amino pyrimidine derivatives in which the pyrimidine ring was 2,4-bis-substituted. Among these derivatives, the compound CYT387 is a selective JAK1 and JAK2 kinase inhibitor, with a chemical name of N-(cyanomethyl)-4-(2-(4-morpholino-phenylamino)pyrimidin-4-yl)benzamide, and is used in the treatment of cancer, myeloproliferative diseases and other related diseases. This compound is now under Phase II clinical trials of treating myeloproliferative diseases.

Although the targeted inhibition of different protein kinases is beneficial for the treatment of kinase-related diseases, the discovery of novel compounds which specifically inhibit certain protein kinases and have druggability such as excellent oral bioavailability is still found challenging. In addition, there are some side effects and drug resistance problems with some of the protein kinase inhibitors currently available on market.

Thus, there is still a need in the art to develop compounds having JAK kinase inhibitory activity or better pharmacodynamic properties.

SUMMARY OF THE INVENTION

The object of the present invention is to provide a class of novel compounds having JAK kinase inhibitory activity and better pharmacodynamic properties, and the use thereof.

In the first aspect of the present invention, it provides a deuterated phenyl amino pyrimidine compound of formula (I), or the crystal form, pharmaceutically acceptable salt, hydrate or solvate thereof:

(I)

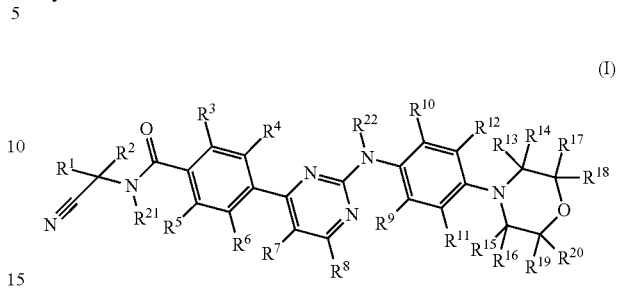

wherein $R^1$, $R^2$, $R^{13}$, $R^{14}$, $R^{15}$, $R^{16}$, $R^{17}$, $R^{18}$, $R^{19}$, $R^{20}$, $R^{21}$ and $R^{22}$ are each independently hydrogen or deuterium; $R^3$, $R^4$, $R^5$, $R^6$, $R^7$, $R^8$, $R^9$, $R^{10}$ and $R^{11}$ are each independently hydrogen, deuterium, halogen, undeuterated C1-C6 alkyl or C1-C6 alkoxy, mono- or multi-deuterated or fully deuterated C1-C6 alkyl or C1-C6 alkoxy, or mono- or multi-halogenated or fully halogenated C1-C6 alkyl or C1-C6 alkoxy;

$R^{12}$ is selected from the group consisting of hydrogen, deuterium, halogen, $OR^{23}$, $COOR^{23}$, $COSR^{23}$, $CONHR^{23}$ or $CON(R^{23})_2$; wherein $R^{23}$ is selected from the group consisting of hydrogen, deuterium, substituted or unsubstituted C1-C6 alkyl or C3-C8 cycloalkyl, wherein the substituent is selected from the group consisting of the following: halogen, cyano, C1-C6 alkyl or C1-C6 alkoxy;

with the proviso that at least one of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, $R^{21}$ or $R^{22}$ is deuterated or deuterium.

In another preferred embodiment, the deuterium isotope content of deuterium in the deuterium substituted position is at least greater than the content of natural isotopic deuterium (about 0.015%), preferably by 30%, more preferably 50%, more preferably 75%, more preferably 95%, more preferably 99%.

In another preferred embodiment, the compound of formula (I) contains at least one deuterium atom, more preferably two deuterium atoms, more preferably four deuterium atoms, more preferably six deuterium atoms.

In another preferred embodiment, $R^1$ and $R^2$ are hydrogen or deuterium.

In another preferred embodiment, $R^{12}$ is hydrogen or deuterium.

In another preferred embodiment, $R^{13}$, $R^{14}$, $R^{15}$ and $R^{16}$ are hydrogen or deuterium.

In another preferred embodiment, $R^{17}$, $R^{18}$, $R^{19}$ and $R^{20}$ are hydrogen or deuterium.

In another preferred embodiment, $R^{13}$, $R^{14}$, $R^{15}$, $R^{16}$, $R^{17}$, $R^{18}$, $R^{19}$ and $R^{20}$ are deuterium.

In another preferred embodiment, $R^3$, $R^4$, $R^5$, $R^6$, $R^7$ or $R^8$ are each independently selected from the group consisting of: hydrogen, deuterium, mono- or multi-deuterated or fully deuterated methyl or methoxyl, or mono- or multi-deuterated or fully deuterated ethyl or ethoxyl.

In another preferred embodiment, $R^3$, $R^4$, $R^5$, $R^6$, $R^7$ or $R^8$ are each independently selected from the group consisting of: mono-deuterated methyl, bi-deuterated methyl, tri-deuterated methyl, mono-deuterated methoxyl, bi-deuterated methoxyl, tri-deuterated methoxyl, mono-deuterated ethyl, bi-deuterated ethyl, tri-deuterated ethyl, tetra-deuterated ethyl, penta-deuterated ethyl, mono-deuterated ethoxyl, bi-deuterated ethoxyl, tri-deuterated ethoxyl, tetra-deuterated ethoxyl, and penta-deuterated ethoxyl.

In another preferred embodiment, the compound is one selected from the group consisting of the following, or the pharmaceutical acceptable salt thereof:

N-(cyano(d₂-methyl))-4-(2-(4-(d₈-morpholino)phenylamino)pyrimidin-4-yl)benzamide;

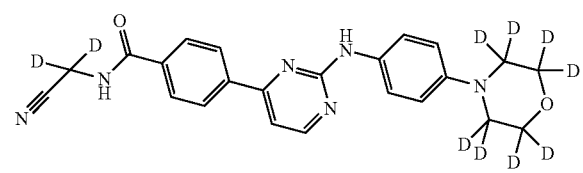 [SMILES: [2H]C([2H])(C#N)NC(=O)c1ccc(-c2ccnc(Nc3ccc(N4C([2H])([2H])C([2H])([2H])OC([2H])([2H])C4([2H])[2H])cc3)n2)cc1]

N-(cyano(d₂-methyl))-4-(2-(4-(2',2',6',6'-d₄-morpholino)phenylamino)pyrimidin-4-yl)benzamide;

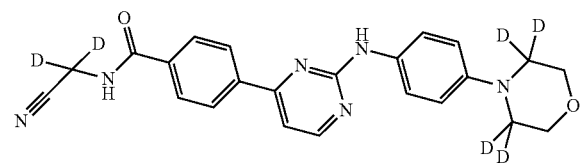 [SMILES: [2H]C([2H])(C#N)NC(=O)c1ccc(-c2ccnc(Nc3ccc(N4C([2H])([2H])COCC4([2H])[2H])cc3)n2)cc1]

N-(cyano(d₂-methyl))-4-(2-(4-(3',3',5',5'-d₄-morpholino)phenylamino)pyrimidin-4-yl)benzamide;

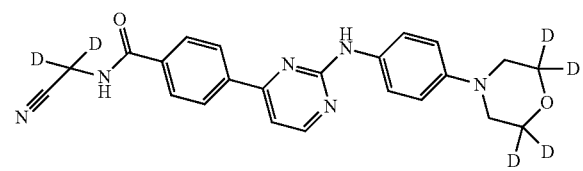 [SMILES: [2H]C([2H])(C#N)NC(=O)c1ccc(-c2ccnc(Nc3ccc(N4CC([2H])([2H])OC([2H])([2H])C4)cc3)n2)cc1]

N-(cyanomethyl)-4-(2-(4-(d₈-morpholino)phenylamino)pyrimidin-4-yl)benzamide;

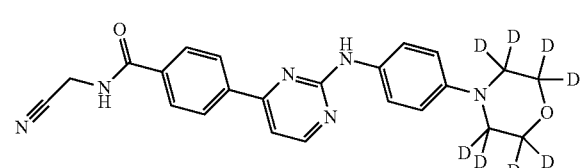

N-(cyanomethyl)-4-(2-(4-(2',2',6',6'-d₄-morpholino)phenylamino)pyrimidin-4-yl)benzamide;

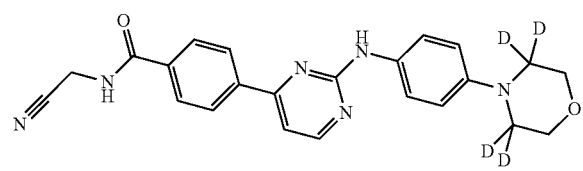 [SMILES: [2H]C1([2H])COCC([2H])([2H])N1c1ccc(Nc2nccc(-c3ccc(C(=O)NCC#N)cc3)n2)cc1]

N-(cyanomethyl)-4-(2-(4-(3',3',5',5'-d₄-morpholino)phenylamino)pyrimidin-4-yl)benzamide;

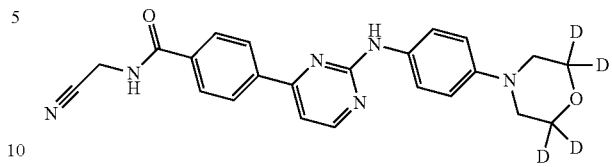

N-(cyano(d₂-methyl))-4-(2-(4-morpholinophenylamino)pyrimidin-4-yl)benzamide;

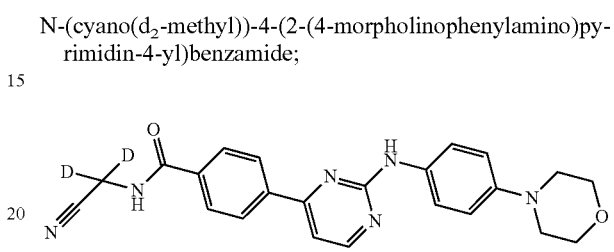

In another preferred embodiment, the compound is

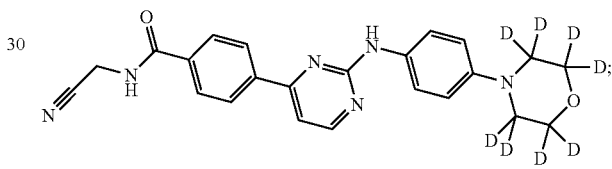

which has the following characteristics: MS calculated: 422. MS found: 423 (M+H)⁺, 445 (M+Na)⁺.

In another preferred embodiment, the compound is

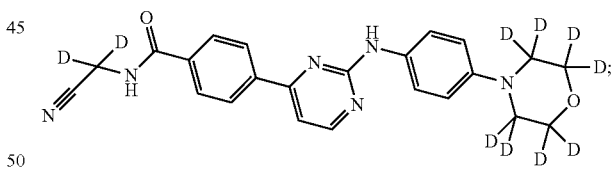

which has the following characteristics: MS calculated: 424. MS found: 425 (M+H)⁺, 447 (M+Na)⁺.

In another preferred embodiment, the compound is

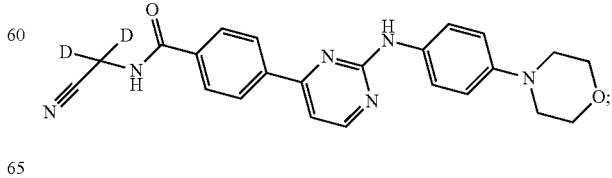

which has the following characteristics: MS calculated: 416. MS found: 417 (M+H)⁺, 439 (M+Na)⁺.

In another preferred embodiment, the compound is

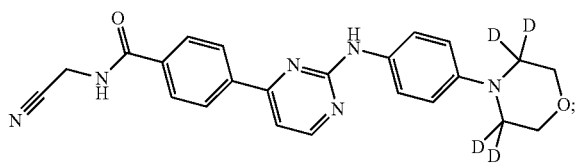 [SMILES: [2H]C1([2H])COCC([2H])([2H])N1c1ccc(Nc2nccc(-c3ccc(C(=O)NCC#N)cc3)n2)cc1]

which has the following characteristics: MS calculated: 418. MS found: 419 (M+H)$^+$, 441 (M+Na)$^+$.

In another preferred embodiment, the compound is

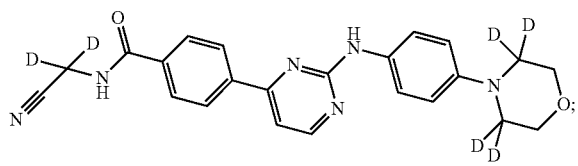 [SMILES: [2H]C([2H])(C#N)NC(=O)c1ccc(-c2ccnc(Nc3ccc(N4C([2H])([2H])COCC4([2H])[2H])cc3)n2)cc1]

which has the following characteristics: MS calculated: 420. MS found: 421 (M+H)$^+$, 443 (M+Na)$^+$.

In another preferred embodiment, the compound does not comprise undeuterated compounds.

In another preferred embodiment, the undeuterated compound is
N-(cyanomethyl)-4-(2-(4-morpholinophenylamino)pyrimidin-4-yl)benzamide.

In another preferred embodiment, the compound is prepared by the method described in Examples 1-8.

In the second aspect of the present invention, it provides a method for preparing pharmaceutical compositions, which comprises the following step: mixing the compound according to the first aspect of the present invention, or a crystal form, pharmaceutically acceptable salt, hydrate or solvate thereof and a pharmaceutically acceptable carrier to form a pharmaceutical composition.

In the third aspect of the present invention, it provides a pharmaceutical composition, which comprises a pharmaceutically acceptable carrier and the compound according to the first aspect of the present invention, or a crystal form, pharmaceutically acceptable salt, hydrate or solvate thereof.

In another preferred embodiment, the pharmaceutical composition is an injection, capsule, tablet, pill, powder or granule.

In another preferred embodiment, the pharmaceutical composition further comprises an additional therapeutic agent which is a medicine for cancer, cardiovascular diseases, inflammation, immune diseases, myeloproliferative diseases, viral diseases, metabolic diseases, or organ transplantation.

More preferably, the additional therapeutic agent comprises (but not limited to): 5-fluorouracil, Avastin™ (avastin, bevacizumab), bexarotene (bexarotene), bortezomib (bortezomib), calcitriol (calcitriol), canertinib (canertinib), capecitabine (capecitabine), carboplatin (carboplatin), celecoxib (celecoxib), cetuximab (cetuximab), cisplatin (cisplatin), dasatinib (dasatinib), digoxin (digoxin), enzastaurin, Erlotinib (Erlotinib), etoposide (etoposide), everolimus (everolimus), fulvestrant (fulvestrant), gefitinib (gefitinib), 2,2-difluoro-deoxycytidine (gemcitabine), genistein (genistein), imatinib (imatinib), irinotecan (irinotecan), lapatinib (lapatinib), lenalidomide (lenalidomide), letrozole (letrozole), folinic acid (leucovorin), matuzumab (matuzumab), oxaliplatin (oxaliplatin), Taxol (paclitaxel), panitumumab (panitumumab), pegylated granulocyte colony stimulating factor (pegfilgrastin), peglated alfa-interferon (peglated alfa-interferon), pemetrexed (pemetrexed), Polyphenon® E, satraplatin (satraplatin), sirolimus (sirolimus), sunitinib (sutent, sunitinib), sulindac acid (sulindac), Taxotere (taxotere), temozolomide (temodar, temozomolomide), Torisel (Torisel), temsirolimus (temsirolimus), tipifarnib (tipifarnib), trastuzumab (trastuzumab), valproic acid (valproic acid), vinflunine (vinflunine), Volociximab, Vorinostat, sorafenib (Sorafenib), ambrisentan (ambrisentan), CD40 and/or CD154-specific antibodies, fusion proteins, NF-kB inhibitors, non-steroidal anti-inflammatory drugs, β-agonists such as salmeterol and blood coagulation factor FXa inhibitors (such as rivaroxaban, etc.), anti-TNF antibody, prostaglandin drugs or montelukast (montelukast).

In the fourth aspect of the present invention, it provides use of the compound of the first aspect of the present invention, or the crystal form, pharmaceutically acceptable salt, hydrate or solvate thereof in the preparation of a pharmaceutical composition for inhibiting protein kinases (e.g. JAK kinases).

In another preferred embodiment, the pharmaceutical composition is used for the treatment and prevention of the following diseases: cancer, myeloproliferative diseases, inflammation, immune diseases, organ transplantation, viral diseases, cardiovascular diseases, or metabolic diseases.

In another preferred embodiment, the cancer includes (but is not limited to): non-small cell lung cancer, uterine cancer, rectal cancer, colon cancer, brain cancer, head cancer, neck cancer, bladder cancer, prostate cancer, breast cancer, renal cancer, leukemia, liver cancer, stomach cancer, thyroid cancer, nasopharyngeal cancer or pancreatic cancer.

In another preferred embodiment, the myeloproliferative diseases include (but are not limited to): spontaneous thrombocythemia (ET), idiopathic myelofibrosis (IMF), chronic myelogenous leukemia (CML), primary myelofibrosis, chronic neutrophilic leukemia (CNL) or polycythemia Vera (PV).

In another preferred embodiment, the inflammation or immune diseases include (but are not limited to): rheumatoid arthritis, osteoarthritis, rheumatoid spondylitis, gout, asthma, bronchitis, rhinitis, chronic obstructive pulmonary disease, cystic fibrosis disease.

In the fifth aspect of the present invention, there is provided a method for inhibiting a protein kinase (e.g. JAK kinases) or for treating diseases (such as cancer, myeloproliferative diseases, inflammation, immune diseases, organ transplantation, viral diseases, cardiovascular diseases or metabolic diseases), which method comprises the following step: administering to a subject in need thereof the compound of the first aspect of the present invention, or a crystal form, pharmaceutically acceptable salt, hydrate or solvate thereof, or administering to a subject in need thereof the pharmaceutical composition of the third aspect of the present invention.

It should be understood that, within the scope of the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through research, the inventor has unexpectedly discovered that the deuterated phenyl amino pyrimidine compounds or the pharmaceutically acceptable salts thereof according to the present invention are remarkably superior to undeuterated compounds in pharmacokinetic and/or pharmacodynamic properties, and therefore more suitable to be used as JAK kinases inhibitory compounds, and thus more suitable to be used in the manufacture of the medicines for treatment of cancer and diseases associated with JAK kinases. The present invention was completed on this basis.

DEFINITIONS

As used herein, "halogen" refers to F, Cl, Br, and I. More preferably, the halogen atom is selected from F, Cl and Br.

As used herein, "C1-C6 alkyl" refers to a straight or branched alkyl which comprises 1 to 6 carbon atoms, such as methyl, ethyl, propyl, isopropyl, butyl, isobutyl, tert-butyl or similar groups.

As used herein, "C1-C6 alkoxy" refers to a straight or branched alkoxy which comprises 1 to 6 carbon atoms, such as methoxy, ethoxy, propoxy, isopropoxy, butoxy, isobutoxy, tert-butoxy, or similar groups.

As used herein, "C3-C8 cycloalkyl" refers to a cycloalkyl which comprises 3 to 8 carbon atoms, such as cyclopropyl, cyclobutyl, cyclopentyl, cyclohexyl, or similar groups.

As used herein, "deuterated" means that one or more hydrogens in the compound or radical are replaced by deuterium. "Deuterated" may be mono-substituted, di-substituted, multi-substituted or fully substituted. The term "one or more deuterated" and "mono- or multi-deuterated" can be used interchangeably.

As used herein, "undeuterated compound" refers to a compound which has a percentage of deuterium atom not higher than the natural isotopic deuterium content (about 0.015%).

In another preferred embodiment, deuterium isotope content of the deuterium substituted position is greater than the natural isotopic deuterium content (0.015%), more preferably greater than the natural isotopic deuterium content by 50%, more preferably 75%, more preferably 95%, more preferably 97%, more preferably 99%, more preferably 99.5%.

In another preferred embodiment, the compound of formula (I) contains at least 2 deuterium atoms, more preferably 4 deuterium atoms, more preferably 6 deuterium atoms, more preferably 8 deuterium atoms.

Preferably, in the compound of formula (I), N is $^{14}$N and/or O is $^{16}$O.

In another preferred embodiment, in the compound, the $^{14}$N isotope content in the nitrogen atom position is ≥95%, preferably ≥99%.

In another preferred embodiment, in the compound, the $^{16}$O isotope content in the oxygen atom position is ≥95%, preferably ≥99%.

DEFINITIONS

As used herein, the term "the compound of the present invention" refers to the compound of formula (I). The term also comprises the crystal forms, pharmaceutically acceptable salts, hydrates or solvates of compound of formula (I).

Wherein the term "pharmaceutically acceptable salt" refers to a salt formed by the compound of the present invention and an acid or base, which is suitable for use as a medicine. The pharmaceutically acceptable salts include inorganic and organic salts. A preferred type of salts is salts formed by the compound of the present invention and an acid. Suitable salt-forming acids include, but are not limited to: inorganic acids such as hydrochloric acid, hydrobromic acid, hydrofluoric acid, sulfuric acid, nitric acid, phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, naphthalenesulfonic acid and the like; and amino acids such as proline, phenylalanine, aspartic acid, glutamic acid. Another preferred type of salts is salts formed by the compound of the present invention and a base, e.g., alkali metal salts (e.g. sodium or potassium salts), alkaline earth metal salts (e.g. calcium or magnesium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bi-hydroxyethylamine salts, tri-hydroxyethylamine salts, and amine salts formed by morpholine, piperazine, and lysine, respectively.

The term "solvate" refers to a complex of specific ratio formed by complexation of the compound of the present invention and a solvent molecule. "Hydrate" refers to a complex formed by complexation of the compound of the present invention and water.

Moreover, the compounds of the present invention further comprise prodrugs of phenylaminopyrimidine compounds of formula (I). The term "prodrug" includes a class of compounds which has biological activity or non-activity and will convert to the compound of formula (I) through metabolism or chemical reactions in the human body when administered by appropriate methods, or a salt or solution formed by a compound of formula (I). The prodrugs include (but are not limited to) the carboxylic acid ester, carbonic ester, phosphate, nitrate, sulfate, sulfone ester, sulfoxide esters, amino compounds, carbamates, azo compounds, phosphoramides, glucoside, ether, acetal of the compound, etc.

Preparation Method

Hereinafter more specifically describes the preparation of compounds of formula (I), but such specific methods do not constitute any limitation to the present invention. The compounds of the invention may also be easily prepared by optionally combine the various synthetic methods described in this specification or known in the art. Such combinations can be easily performed by one of ordinary skill in the art of the present invention.

The methods of preparing the undeuterated phenylaminopyrimidine compounds and the physiologically compatible salts thereof used in the present invention are known in the art. Preparation of corresponding deuterated phenylaminopyrimidine compounds can be conducted by using the corresponding deuterated compound as starting materials, and synthesizing by the same route. For example, a compound of formula (I) of the present invention can be prepared according to the method described in WO2008109943, except that the deuterated material is used instead of the non-deuterated material.

Generally, in the preparation process, each reaction is generally conducted in an inert solvent, under room temperature to reflux temperature (such as 0° C.~80° C., preferably from 0° C.~50° C.). The reaction time is usually 0.1 hours-60 hours, preferably 0.5 to 48 hours.

The following general preparative route may be used in the synthesis of compounds of formula (I) of the present invention.

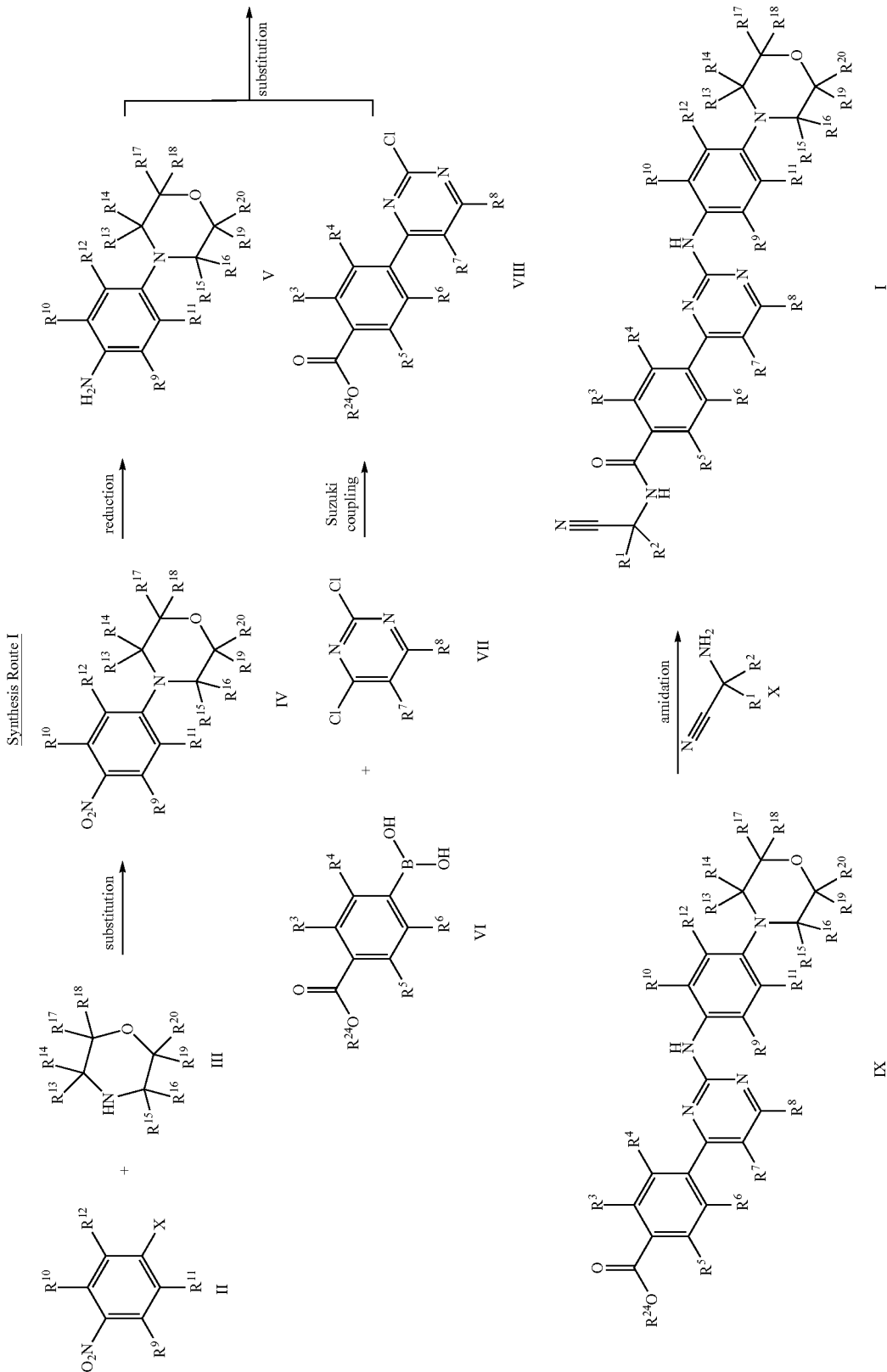

Wherein, X is selected from F, Cl, Br, I; the definitions of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ or $R^{20}$ are as above; $R^{24}$ is selected from hydrogen, and C1-C6 alkyl.

As shown in the synthesis route I, the nitrobenzenes compound II and the morpholine compound III react to produce 4-morpholino substituted nitrobenzenes compound IV, which is then reduced to obtain 4-morpholino substituted phenylamine compound V. The phenylboronic acid compound VI and the 2,4-dichloropyrimidine compound VII produce compound VIII by Suzuki coupling. Compound VIII react with compound V to obtain phenylaminopyrimidine compound IX. Compound IX and the aminoacetonitrile compound X produce Compound I of the present invention by amidation reaction. The above reactions are conducted in inert solvents, such as dichloromethane, dichloroethane, acetonitrile, n-hexane, toluene, tetrahydrofuran, N, N-dimethylformamide, dimethyl sulfoxide, etc, and under the temperature of 0-200° C.

Pharmaceutical Composition and Administration Methods

The compounds of the present invention possess outstanding activity of inhibiting protein kinase (such as JAK kinases). Therefore, the compounds of the present invention, and the various crystal forms, pharmaceutically acceptable inorganic or organic salts, hydrates or solvates thereof, and the pharmaceutical composition comprising the compound of the present invention as a main active ingredient can be used for treating, preventing and alleviating diseases mediated by protein kinases (e.g. JAK kinases). Based on the prior art, the compounds of the invention can treat the following diseases: cancer, myeloproliferative diseases, inflammation, immune diseases, organ transplantation, viral diseases, cardiovascular diseases or metabolic diseases etc.

The pharmaceutical composition of the invention comprises the compound of the present invention or the pharmaceutically acceptable salts thereof in a safe and effective amount and pharmaceutically acceptable excipients or carriers. Wherein, the term "safe and effective dosage" refers to the amount of the compounds which is enough to improve the patient's condition without any serious side effect. Generally, the pharmaceutical composition contains 1-2000 mg of the compound of the invention per dose, preferably, 10-200 mg of the compound of the invention per dose. Preferably, "per dose" means one capsule or tablet.

"Pharmaceutically acceptable carrier" means one or more compatible solid or liquid fillers or gel materials, which are suitable for human use, and must have sufficient purity and sufficiently low toxicity. "Compatibility" herein means that the components of the compositions can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation for administration modes of the compounds or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one of the conventional inert excipients (or carriers), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in a given portion of the digestive tract. Examples of the embedding components include polymers and waxes. If necessary, the active compounds and one or more of the above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and fragrance.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administered alone, or in combination with any other pharmaceutically acceptable compounds.

When the pharmaceutical compositions are used, a safe and effective amount of compound of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

Compared to non-deuterated compounds known in the prior art, the compounds of the present invention possess a number of advantages. Main advantages of the present invention comprise:

(1) The compounds of the present invention have an excellent inhibitory activity to protein kinase (such as JAK kinase).

(2) The metabolism of the deuterated compounds in the organism is changed by deuterate technology, thus conferring the compounds better pharmacokinetic parameter characteristic. In this case, the dose may be varied and a long-acting preparation can be formed to improve the applicability.

(3) The hydrogen in the compounds has been substituted with deuterium, the drug concentration of the compound in animals can be enhanced due to the deuterium isotope effect, thereby improving drug efficacy.

(4) The hydrogen in the compounds has been substituted with deuterium, and since some metabolites are suppressed, the safety of the compounds may be improved.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight. In the present invention, "biotin" means biotin.

Example 1 the preparation of N-(cyanomethyl)-4-(2-(4-(d$_8$-morpholino)phenyl amino)pyrimidine-4-yl)benzamide (compound 9)

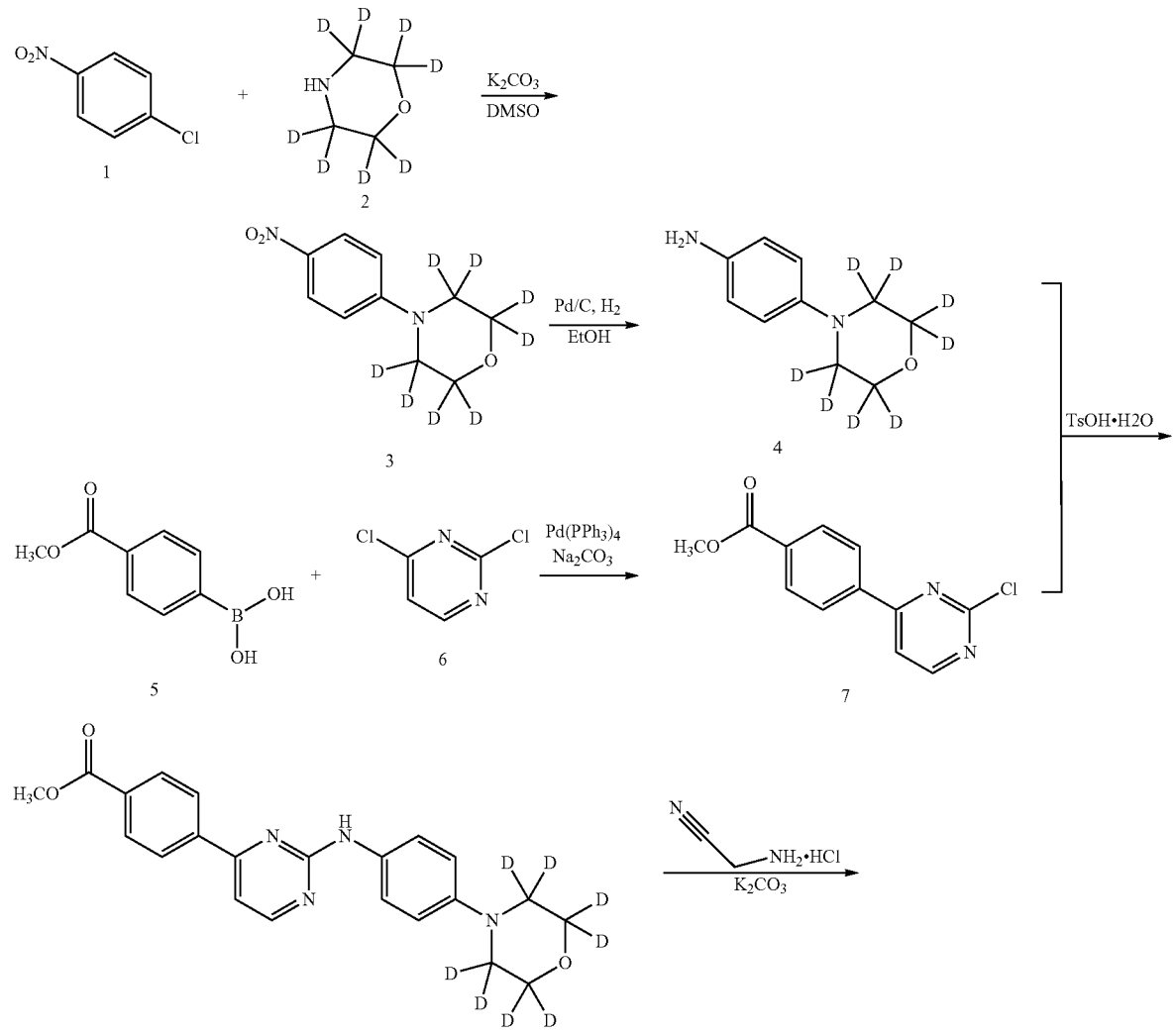

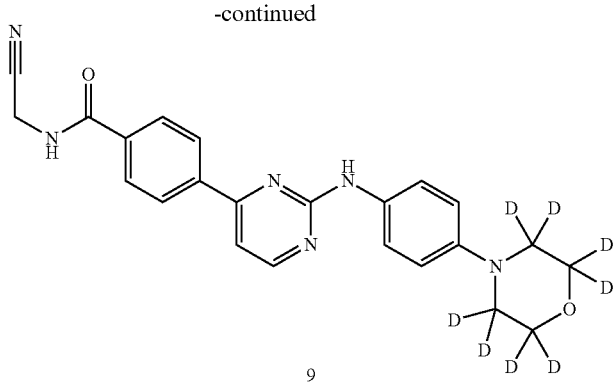

9

1. The preparation of 4-(4-nitrophenyl)(d₈-morpholine) (compound 3)

Compound 4-chloronitrobenzene (3.53 g, 22.4 mmol), d₈-morpholine (2.35 g, 24.6 mmol) and potassium carbonate (6.07 g, 44 mmol) were added into a flask sequentially, and dimethylsulfoxide (40 mL) was added. After that, it was heated up to 100° C. and was stirred for 16 h. TLC analysis (ethyl acetate/petroleum ether=1/10) showed that the reaction has completed. Then it was cooled to room temperature, and the reaction was quenched by adding water (100 mL). It was extracted by dichloromethane (100 mL) for two times. The combined organic layer was washed with water and saturated brine, dried with anhydrous sodium sulfate, filtered and concentrated under vacuum by rotary evaporator to give the crude product. It was crystallized in the mixed solvent of ethyl acetate and n-hexane (1/5, v/v, 18 mL) to obtain the yellow solid desired product (3.92 g, yield 81%); MS Calcd.: 216; MS Found: 217 (M+H)⁺.

2. The preparation of 4-(d₈-morpholino)phenylamine (compound 4)

4-(4-nitrophenyl) (d₈-morpholino)(3.80 g, 17.6 mmol), ethanol (30 mL) and water (3 mL) were added into a hydrogenation bottle. 10% palladium on carbon (0.19 g) was added under nitrogen protection. The reaction system was replaced with hydrogen for 3-4 times, and was stirred under 10 atm hydrogen pressure, and stirred to react under 40° C. for 10 hours. HPLC detected that the reaction has completed, and then the reaction solution was cooled to room temperature, and filtered through Celite. The residue was washed with ethanol. The filitrate was combined and concentrated under vacuum by rotary evaporator to give the desired product, offwhite solid (3.11 g, yield: 95%). MS Calcd.: 186; MS Found: 187 (M+H)⁺.

3. The preparation of 4-(2-chloropyrimidin-4-yl)methyl benzoate (compound 7)

Compound 4-(methoxycarbonyl)phenylboronic acid (4.28 g, 23.78 mmol), 2,4-dichloropyrimidine (3.72 g, 24.97 mmol), toluene (40 mL) and sodium carbonate aqueous solution (2N, 11.9 mL) was added into a flask sequencially. Tetrakis(triphenylphosphine) palladium (1.10 g, 0.95 mmol) was added under nitrogen protection, heated to 80° C. and stirred overnight. After cooled to room temperature, water (10 mL) and ethyl acetate (50 mL) were added to dilute the reaction solution, stirred for 15 min and layered. Then ethyl acetate (30 mL) was used to extract the aqueous layer for two times. The combined organic layer was washed with water and brine. Dried with anhydrous sodium sulfate, filtered and concentrated under vacuum by rotary evaporator to give the crude product. The crude product was suspended in methanol (10 mL) and was pulped for 30 mins, filtered and washed by methanol. Dried in vacuum to give the desired product, gray solid (3.13 g, yield: 53%). MS Calcd.: 248; MS Found: 249 (M+H)⁺, 271 (M+Na)⁺.

4. The preparation of 4-(2-(4-(d₈-morpholino)phenylamino)pyrimidin-4-yl)methyl benzoate (compound 8)

4-(2-chloro pyrimidine-4-yl)methyl benzoate (1.24 g, 5.0 mmol), 4-(d₈-morpholino)phenylamine (0.84 g, 4.5 mmol) and 1,4-dioxane (10 mL) were added into a flask sequencially. P-toluenesulfonic acid monohydrate (0.88 g, 5.0 mmol) was added into the above suspension under stirring. Heated to reflux for 48 h, then cooled to 30° C., and the reaction mixture was concentrated under vacuum by rotary evaporator. Ethyl acetate (20 mL) and aqueous sodium bicarbonate solution (20 mL) was added and layered. The aqueous layer was extracted with ethyl acetate for twice. The combined organic layer was washed with water, saturated aqueous sodium bicarbonate and brine, dried with anhydrous sodium sulfate, filtered and concentrated under vacuum with rotary evaporator to give crude product. The crude product is purified by column chromatography to give a yellow solid, suspended in methanol (5 mL), and pulped for 15 min. After filteration, the residue was washed with methanol, and dried under vacuum to give the desired product (1.09 g, yield: 61%). MS Calcd.: 398; MS Found: 399 (M+H)⁺, 421 (M+Na)⁺.

5. The preparation of N-(cyanomethyl)-4-(2-(4-(d₈-morpholino)phenylamino)pyrimidin-4-yl)benzamide (compound 9)

4-(2-(4-(d₈-morpholino)phenylamino)pyrimidin-4-yl) methyl benzoate (0.50 g, 1.25 mmol), anhydrous potassium carbonate (325 mesh, 0.35 g, 2.5 mmol) and tetrahydrofuran (4 mL) were added to a flask sequencially under nitrogen protection. 2-amino-acetonitrile hydrochloride (0.18 g, 1.88 mmol) was added under stirring. Then reacted for 13-17 h with the internal reaction temperature maintained at 35±2° C., and the reaction was monitored with HPLC until it has completed. Purified water (10 mL) was added, and the reaction solution was concentrated under vacuum with rotary evaporator, then extracted with ethyl acetate for three times. The combined organic layer was washed with water and brine. Dried with anhydrous sodium sulfate, filtered, and was concentrated under vacuum with rotary evaporator to give crude product. The crude product was purified by column chromatography to provide a solid desired product 5 (0.21 g, yield: 40%). MS Calcd.: 422; MS Found: 423 (M+H)$^+$, 445 (M+Na)$^+$.

Example 2

The preparation of N-(cyanomethyl)-4-(2-(4-($d_8$-morpholino)phenyl amino)pyrimidine-4-yl)benzamide (compound 9)

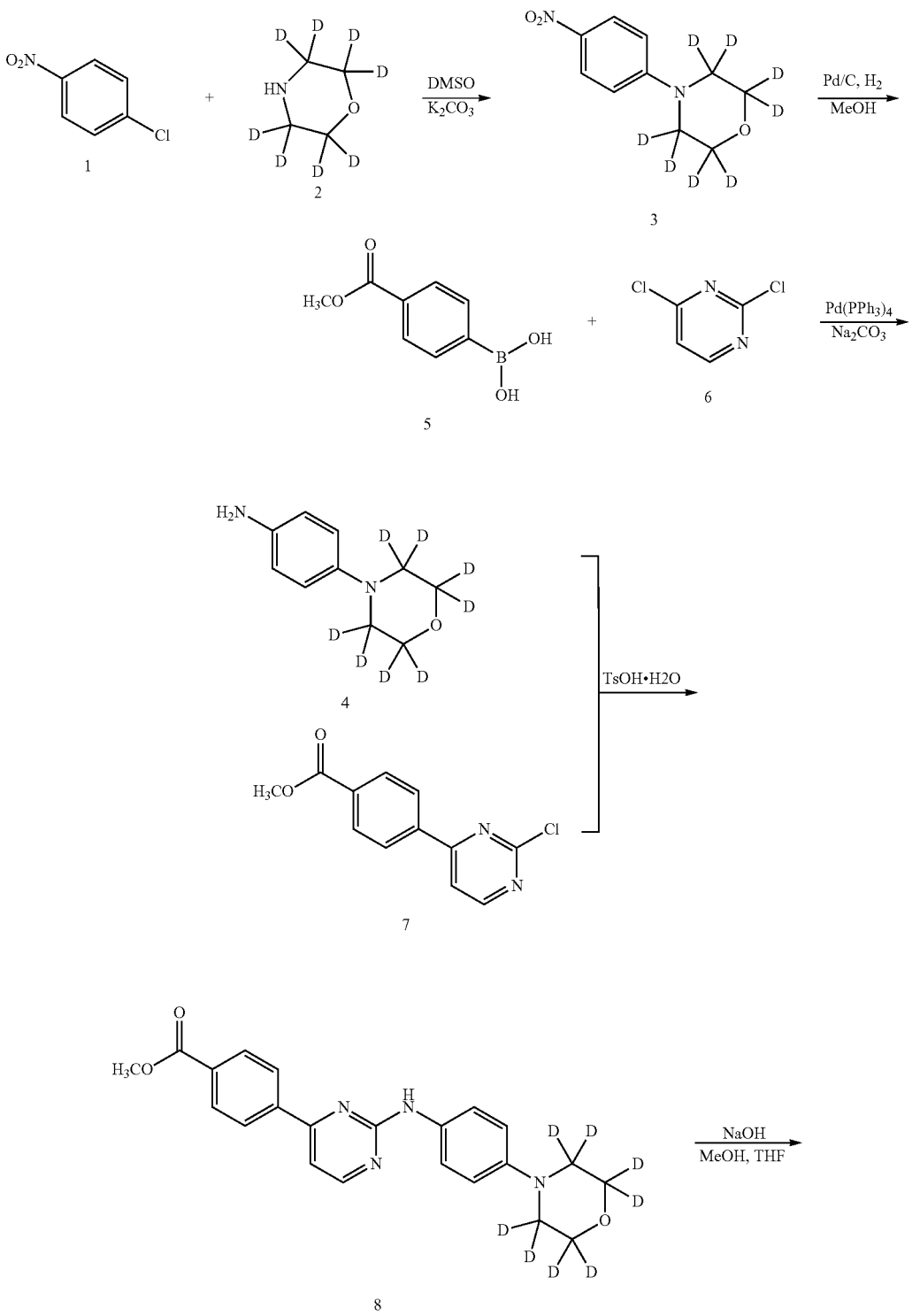

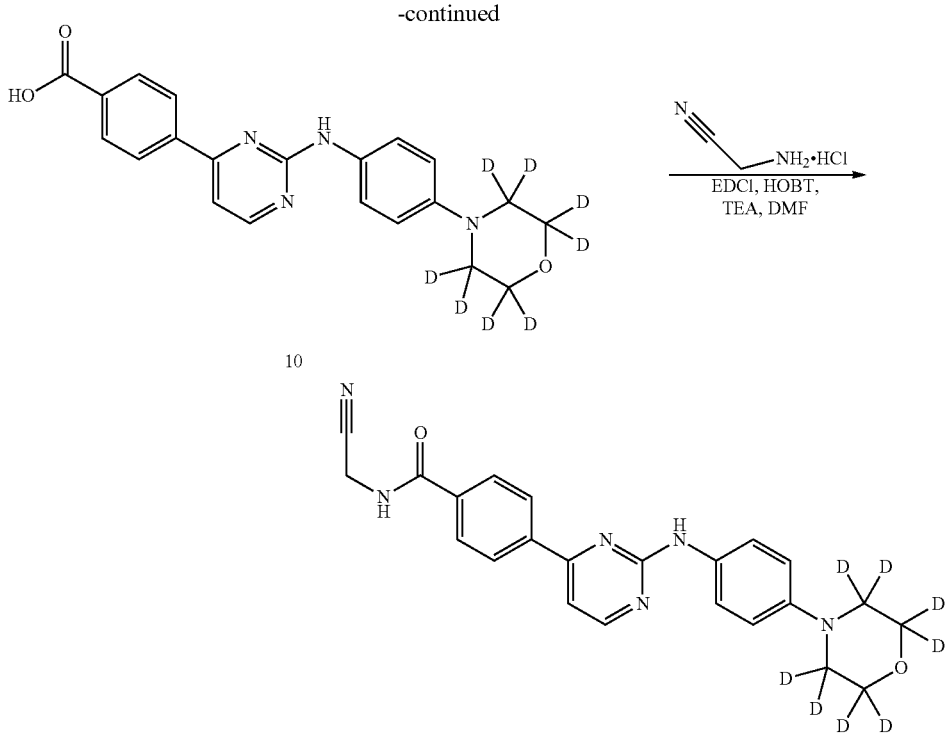

1. The preparation of 4-(4-nitrophenyl) ($d_8$-morpholine) (compound 3)

4-chloronitrobenzene (0.662 g, 4.17 mmol), $d_8$-morpholine (0.400 g, 4.17 mmol, purchased from Cambridge Isotope Laboratories) and potassium carbonate (1.733 g, 12.54 mmol) were added to a flask sequencially. Dimethylsulfoxide (6 mL) was added, then heated to 100° C., and stirred for 20 hours. The reaction mixture was cooled to room temperature, then water (30 mL) was added to quench the reaction, and there was yellow solid precipitated. After stirred for 30 min, the mixture was filtered to obtain the crude product. The crude product was crystallized in the mixed solvent of ethyl acetate and petroleum ether (1/2.5, v/v, 14 mL) to obtain the yellow solid desired product (0.600 g, HPLC purity: 98.6%, yield 67%).

2. The preparation of 4-($d_8$-morpholino)phenylamine (compound 4)

4-(4-nitrophenyl) ($d_8$-morpholino) (0.600 g, 2.78 mmol) and methanol (40 ml) were added to the hydrogenation reaction vessel. 10% palladium on carbon (0.060 g) was added under nitrogen protection. The reaction system was replaced with hydrogen for 3-4 times, and was stirred under hydrogen pressure, and stirred to react under 40° C. for 20 hours. HPLC detected that the reaction has completed, and then the reaction solution was cooled to room temperature, and filtered through Celite. The residue was washed with methanol. The combined filtrate was concentrated under vacuum by rotary evaporator to give the desired product, pink solid (0.500 g, HPLC purity: 98.1%, yield: 96.5%).

3. The preparation of 4-(2-chloropyrimidin-4-yl)methyl benzoate (compound 7)

4-(methoxycarbonyl)phenylboronic acid (4.000 g, 22.23 mmol), 2,4-dichloropyrimidine (3.150 g, 21.11 mmol), toluene (40 mL) and sodium carbonate aqueous solution (2 N, 10.5 mL) were added to a flask. Tetrakis(triphenylphosphine) palladium (0.513 g, 0.45 mmol) was added under nitrogen protection, heated to 80° C. and stirred overnight. After cooled to room temperature, water (10 mL) and ethyl acetate (50 mL) were added to dilute the reaction solution, stirred for 15 min and layered. The aqueous layer was extracted with ethyl acetate (30 mL) for two times. The combined organic layer was washed with water and brine, dried with anhydrous sodium sulfate, filtered and concentrated under vacuum by rotary evaporator to give the crude product. The crude product was separated and purified by Silica gel column chromatography (ethyl acetate/petroleum ether=0-30%), dried under vacuum to obtain the white solid desired product (2.50 g, yield: 48%). $^1$H NMR (400 MHz, CDCl3) δ 8.71-8.70 (1H, d), 8.19-8.14 (4H, m), 7.71-7.70 (1H, d), 3.97 ppm (3H, s).

4. The preparation of 4-(2-(4-($d_8$-morpholino)phenylamino)pyrimidin-4-yl)methyl benzoate (compound 8)

4-(2-chloropyrimidin-4-yl)methyl benzoate (0.606 g, 2.44 mmol), 4-($d_8$-morpholino)phenylamine (0.500 g, 2.68 mmol) and 1,4-dioxane (25 mL) were added to a flask. P-toluenesulfonic acid monohydrate (0.510 g, 2.68 mmol) was added to the suspension under stirring. Heated to reflux for 20 h, then the reaction mixture was concentrated under vacuum by rotary evaporator. Ethyl acetate (15 mL) and 5% aqueous sodium bicarbonate (15 mL) were added, and there was yellow solid precipitated. After stirred for 30 mins, the mixture was filtered to obtain the crude product. The crude product was suspended in methanol (5 mL), and pulped for 5 mins, filtered, and the residue was washed by methanol, dried under vacuum to obtain the solid desired product (0.680 g, HPLC purity: 95%, yield: 70%).

5. 4-(2-(4-($d_8$-morpholino)phenylamino)pyrimidin-4-yl)benzoic acid (compound 10)

4-(2-(4-($d_8$-morpholino)phenylamino)pyrimidin-4-yl) methyl benzoate (0.680 g, 1.706 mmol), sodium hydroxide (0.137 g, 3.413 mmol), water (3.5 ml), and the mixed solvent of methanol and tetrahydrofuran (12 mL, 3:1) were added to the flask, heated to 65° C. and reacted for 2 h. The reaction mixture was cooled to room temperature. The solvent was removed and the pH was adjusted to 3 by 10% diluted hydrochloric acid, filtered and dried to obtain grey solid. The crude product was grinded to powder, and methanol (5 mL) was added, pulped for 5 min, then filtered and dried to obtain solid desired product (0.570 g, HPLC purity: 98.3%, yield: 87%).

6. The preparation of N-(cyanomethyl)-4-(2-(4-($d_8$-morpholino)phenylamino)pyrimidin-4-yl)benzamide (compound 9)

4-(2-(4-($d_8$-morpholino)phenylamino)pyrimidin-4-yl) benzoic acid (0.300 g, 0.780 mmol), 1-ethyl-(3-dimethylaminopropyl) carbodiimide hydrochloride (0.180 g, 0.936 mmol), 1-hydroxy-phenylpropyl triazole (0.127 g, 0.936 mmol), triethylamine (0.473 g, 4.682 mmol) and N, N-dimethylformamide (3 mL) were added to a flask under nitrogen protection. 2-amino-acetonitrile hydrochloride was added under stirring, and reacted for 20 h under room temperature. Purified water (5 mL) and saturated bicarbonate solution (5 mL) were added to the reaction mixture, and there was yellow solid precipitated. After stirred for 30 mins, it was filtered and washed by clear water. The crude product was obtained after drying, and was separated by separation and purification with preparative chromatography to obtain yellow solid desired product (0.150 g, HPLC purity: 98.1%, yield: 45%). MS Calcd.: 422; MS Found: 423 (M+H)$^+$. $^1$H NMR (400 MHz, DMSO-$d_6$) δ 9.65 (1H, s), 9.38-9.35 (1H, m), 8.57-8.56 (1H, d), 8.29-8.27 (2H, d), 8.05-8.03 (2H, d), 7.75-7.72 (2H, d), 7.46-7.45 (1H, d), 7.09-7.07 (2H, m), 4.37-4.36 ppm (2H, d).

Example 3

The preparation of N-(cyano($d_2$-methyl))-4-(2-(4-($d_8$-morpholino)phenylamino)pyrimidin-4-yl)benzamide (compound 13)

1. The preparation of 2-amino-2,2-$d_2$-acetonitrile hydrochloride (compound 12)

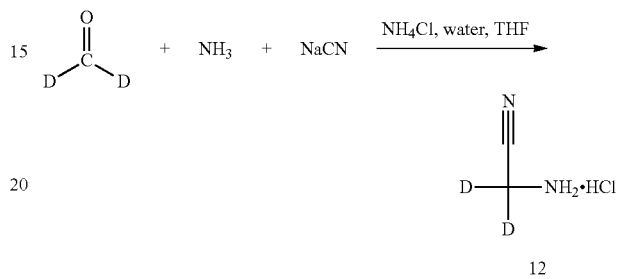

Sodium cyanide (1.59 g, 32.46 mmol) and ammonia (6.80 g, 99.87 mmol) was added to the flask under ice bath, the inner temperature was controlled under 5° C., and ammonium chloride (2.27 g, 42.25 mmol) was added. After 10 min of stirring, deuterated formaldehyde (1.00 g, 31.21 mmol) was slowly added dropwise in 10 mins, and the inner temperature was controlled to be 16-20° C. After stirred under heat-preservation for 3 h, dichloromethane (100 ml) was added and stirred for 45 min, and liquid separated to obtain organic phase. The aqueous phase was extracted twice with dichloromethane (100 ml×2), the combined organic phase was dried over anhydrous sodium sulfate, and filtered. A solution of hydrogen chloride in isopropanol (15 mL) was added to the filtrate under ice bath, and was stirred for 30 mins and there was white solid precipitated. Filtered to obtain white solid desired product (1.70 g, yield: 58%). $^1$H NMR (400 MHz, DMSO-$d_6$) δ 9.12 ppm (3H, s).

2. The preparation of N-(cyano($d_2$-methyl))-4-(2-(4-($d_8$-morpholino)phenylamino)pyrimidin-4-yl)benzamide; (compound 13)

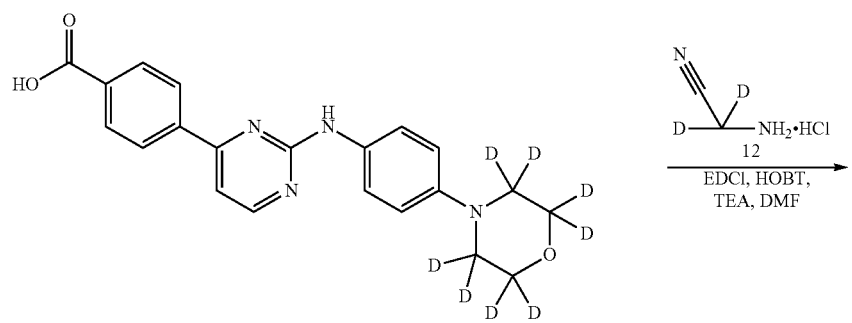

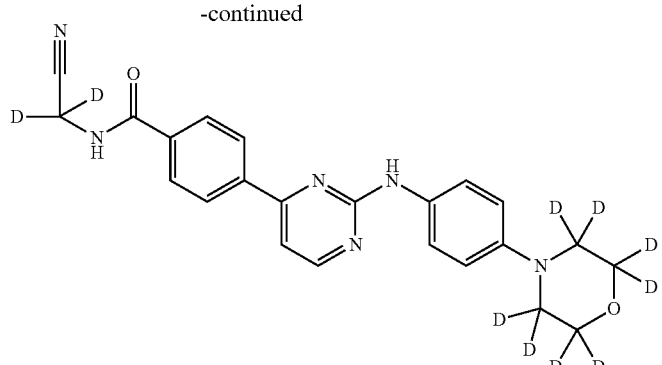

13

4-(2-(4-(d$_8$-morpholino)phenylamino)pyrimidin-4-yl)benzoic acid (0.260 g, 0.676 mmol), 1-ethyl-(3-dimethylaminopropyl) carbodiimide hydrochloride (0.156 g, 0.811 mmol), 1-hydroxyphenylpropyl triazole (0.109 g, 0.811 mmol), triethylamine (0.410 g, 4.056 mmol) and N,N-dimethylformamide (2.5 mL) were added to a flask under nitrogen protection. 2-amino-2,2-d$_2$-acetonitrile hydrochloride (0.192 g, 2.029 mmol) was added under stirring. The reaction was conducted for 19 h under room temperature. Purified water (3 mL) and saturated bicarbonate solution (3 mL) were added to the reaction mixture, and there was yellow solid precipitated. After 30 mins of stirring, the precipitate was filtered and washed with clear water, and dried to obtain crude product. The crude product was purified by preparative chromatography to obtain yellow solid desired product (0.192 g, HPLC purity: 98.2%, yield: 67%). MS Calcd.: 424; MS Found: 425 (M+H)$^+$. $^1$H NMR (400 MHz, DMSO-d$_6$) δ 9.65 (1H, s), 9.35 (1H, s), 8.57-8.56 (1H, d), 8.29-8.27 (2H, d), 8.05-8.03 (2H, d), 7.74-7.73 (2H, d), 7.45 (1H, s), 7.09 ppm (2H, s).

Example 4

The preparation of N-(cyano(d$_2$-methyl))-4-(2-(4-(2',2',6',6'-d$_4$-morpholino)phenylamino)pyrimidin-4-yl)benzamide (compound 24)

1. The preparation of 2,2,6,6-d$_4$-morpholine (compound 19)

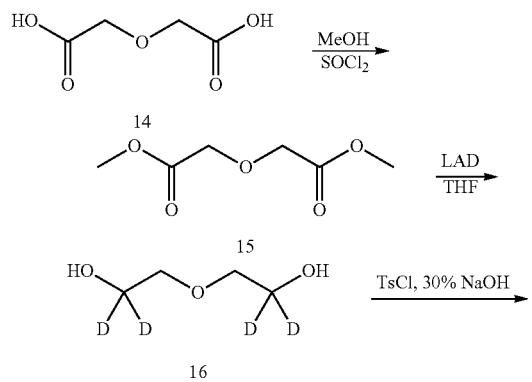

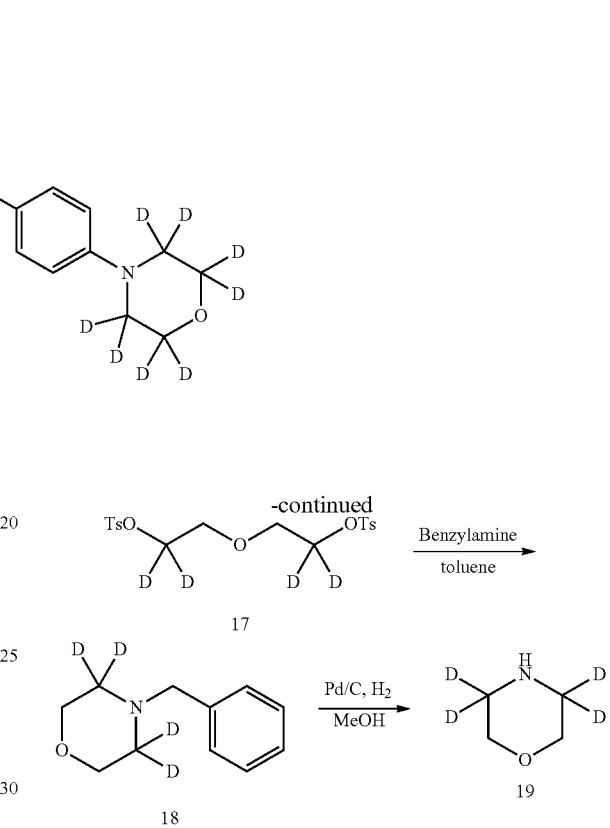

1) The Preparation of Diglycolic Acid Dimethyl Ester (Compound 15)

Diglycolic acid (3.00 g, 22.37 mmol) and anhydrous methanol (30 mL) were added to a flask under ice bath, and dimethylsulfoxide (7.98 g, 67.12 mmol) was slowly added dropwise, after that, heated to room temperature and stirred for 20 h. The reaction mixture was concentrated to obtain colorless oily desired product (2.50 g, HPLC purity: 97.3%, yield 69%). $^1$H NMR (400 MHz, CDCl$_3$) δ 4.25 (4H, s), 3.76 ppm (6H, s).

2) The preparation of 2,2'-oxy-bis(1,1-d$_2$-ethanol) (compound 16)

Deuterated lithium aluminum hydride (1.49 g, 35.5 mmol, purchased from J&K) and anhydrous tetrahydrofuran (10 mL) was added to the flask under protection of nitrogen, cooled to 0° C. by ice bath, and diglycolic acid dimethyl ester (2.5 g, 15.4 mmol) in tetrahydrofuran (15 mL) solution was slowly added dropwise. After that, the mixture was heated to 65° C., stirred to react for 2 h, then cooled to room temperature and stirred overnight. The reaction mixture was added with 5 mL of water, 2.5 mL of 15% aqueous sodium hydroxide solution, stirred for 30 min and filtered, washed with tetrahydrofuran (20 mL). The filterate was concentrated to obtain the yellow oily desired product (1.50 g, HPLC purity: 92%, yield 88%). $^1$H NMR (400 MHz, CDCl$_3$) δ 3.59 ppm (4H, s).

3) The preparation of 2,2'-oxy-bis(1,1-d$_2$-ethan-2,1-diyl)bis(4-p-toluenesulfonate) (compound 17)

2,2'-oxy-bis(1,1-d$_2$-ethanol)(1.49 g, 35.5 mmol) and 30% aqueous sodium hydroxide (10 mL) were added to the flask under ice bath, and p-toluenesulfonyl chloride (2.5 g, 15.4 mmol) in tetrahydrofuran (15 mL) was slowly added dropwise. After that, the mixture was heated to room temperature and stirred overnight. The reaction mixture was added with water, and extracted with ethyl acetate for three times, and the organic phase was dried on anhydrous sodium sulfate, concentrated to obtain white solid desired product (4.2 g, yield 79%); $^1$H NMR (400 MHz, CDCl$_3$) δ 7.82-7.79 (4H, d), 7.38-7.36 (4H, d), 3.62 (4H, s), 2.48 ppm (6H, s).

4) The preparation of 4-benzyl-2,2,6,6-d$_4$-morpholine (compound 18)

2,2'-oxy-bis(1,1-d$_2$-ethan-2,1-diyl)bis(4-p-toluenesulfonates) (4.20 g, 10.04 mmol), benzylamine (5.37 g, 50.17 mmol) and toluene (40 mL) were added to a flask under ice bath, heated to reflux and reacted for 18 h. The reaction mixture was added with water, and extracted with ethyl acetate for three times, and the organic phase was dried on anhydrous sodium sulfate, concentrated to obtain the crude product. The crude product was separated and purified by column chromatography to obtain white solid desired product (1.3 g, HPLC purity: 91%, yield 72%); $^1$H NMR (400 MHz, CDCl$_3$) δ 7.36-7.28 (5H, m), 3.73 (4H, s), 3.53 ppm (2H, s).

5) The preparation of 2,2,6,6-d$_4$-morpholine (compound 19)

4-benzyl-2,2,6,6-d$_4$-morpholine (1.30 g, 7.17 mmol), palladium hydroxide (0.26 g, 20%) and methanol (13 mL) was added to the flask under hydrogen atmosphere, and was heated to 40° C. After 3 days of reaction, the reaction mixture was cooled to room temperature, filtered, and concentrated to obtain yellow oily desired product (0.4 g, yield 61%).

2. The preparation of N-(cyano(d$_2$-methyl))-4-(2-(4-(2',2',6',6'-d$_4$-morpholino)phenylamino)pyrimidin-4-yl)benzamide (compound 24)

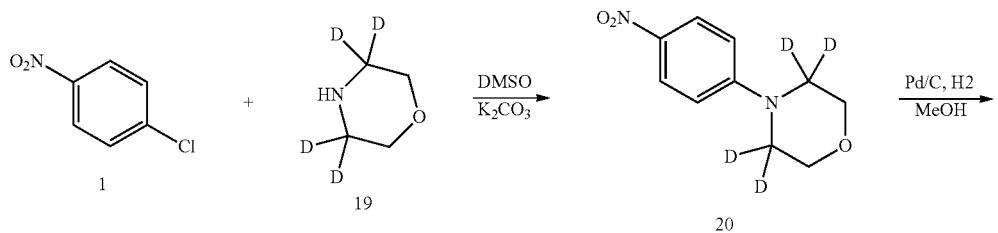

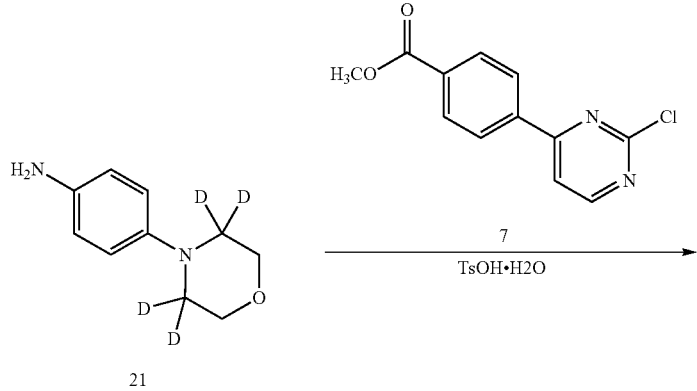

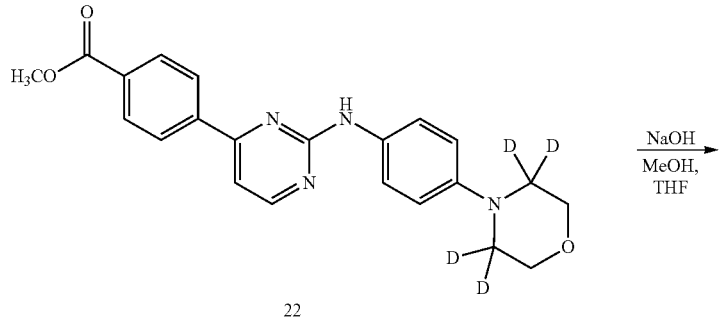

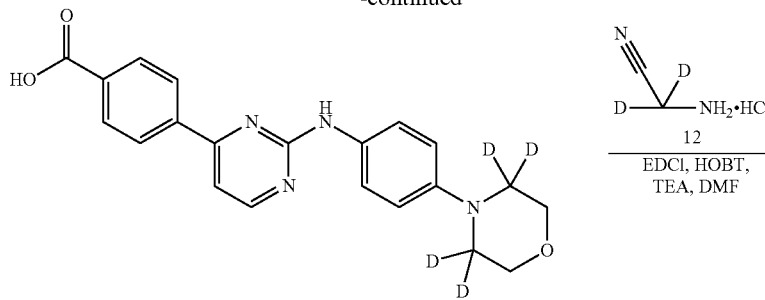

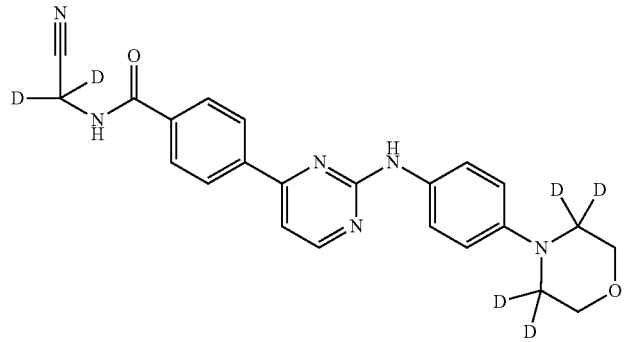

1). The preparation of 4-(4-nitrophenyl) (2',2',6',6'-d₄-morpholino) (compound 20)

4-chloronitrobenzene (0.402 g, 4.411 mmol), 3,3,5,5-d₄-morpholine (0.694 g, 4.411 mmol) and potassium carbonate (1.830 g, 13.233 mmol) were added to a flask. Dimethylsulfoxide (6 mL) was added, after that, heated to 100° C. and stirred for 18 h. The reaction was monitored by HPLC. After the reaction was qualified, the reaction mixture was cooled to room temperature, and was quenched by adding water (30 mL). There was yellow solid precipitated, filtered to obtain the crude product after stirred for 30 mins. The crude product was crystallized in the mixed solvent of ethyl acetate and petroleum ether (1/2.5, v/v, 11 mL) to obtain yellow solid desired product (0.600 g, HPLC purity: 99.5%, yield 64%).

2). The preparation of 4-(2',2',6',6'-d₄-morpholino) phenylamine (compound 21)

4-(4-nitrophenyl) (2',2',6',6'-d₄-morpholino) (0.600 g, 2.827 mmol) and methanol (60 ml) were added to the hydrogenation reaction vessel. 10% Palladium on carbon (0.060 g) was added under nitrogen protection. The reaction system was replaced with hydrogen for 3-4 times, and was stirred under hydrogen pressure to react for 20 hours at 40° C. HPLC detected that the reaction has completed, and then the reaction solution was cooled to room temperature, and filtered through Celite. The residue was washed with methanol. The combined organic layer was concentrated under vacuum by rotary evaporator to give the solid desired product (0.420 g, HPLC purity: 95%, yield: 82%).

3). The preparation of 4-(2-(4-(2',2',6',6'-d₄-morpholino)phenylamino)pyrimidin-4-yl)methyl benzoate (compound 22)

4-(2-chloropyrimidin-4-yl)methyl benzoate (0.521 g, 2.096 mmol), 4-(2',2',6',6'-d₄-morpholino)phenylamine (0.420 g, 2.306 mmol) and 1,4-dioxane (20 mL) were added to a flask. P-toluenesulfonic acid monohydrate (0.439 g, 2.306 mmol) was added to the suspension under stirring. After heated to reflux for 20 h, the reaction mixture was concentrated under vacuum by rotary evaporator. Ethyl acetate (5 mL) and 5% aqueous sodium bicarbonate (5 mL) were added, yellow solid was precipitated, after stirred for 30 min, filtered to give the crude product. The crude product was suspended in methanol (5 mL), pulped for 5 min, and filtered. The residue was washed with methanol, dried under vacuum to obtain solid desired product (0.400 g, HPLC purity: 92%, yield: 48%).

4). 4-(2-(4-(2',2',6',6'-d₄-morpholino)phenylamino) pyrimidin-4-yl)benzoic acid (compound 23)

4-(2-(4-(2',2',6',6'-d₄-morpholino)phenylamino)pyrimidin-4-yl)methyl benzoate (0.400 g, 1.01 mmol), sodium hydroxide (0.008 g, 2.02 mmol), water (3 ml), the mixed solvent of methanol and tetrahydrofuran (12 mL, 3:1) were added to the flask, heated to 65° C., and reacted for 2 h. The reaction mixture was cooled to room temperature, the solvent was removed, and the pH was adjusted to 3 by 10% diluted hydrochloric acid, filtered and dried to obtain grey solid. The crude product was grinded to powder. Methanol (5 mL) was added and pulped for 5 min, and then filtered and dried to obtain solid desired product (0.340 g, HPLC purity: 92%, yield: 88%).

5). The preparation of N-(cyano(d₂-methyl)-4-(2-(4-(2',2',6',6'-d₄-morpholino)phenylamino)pyrimidin-4-yl)benzamide (compound 24)

4-(2-(4-(2',2',6',6'-d₄-morpholino)phenylamino)pyrimidin-4-yl)benzoic acid (0.170 g, 0.447 mmol), 1-ethyl-(3-dimethylaminopropyl) carbodiimide hydrochloride (0.103 g, 0.536 mmol), 1-hydroxyphenylpropyl triazole (0.724 g, 0.536 mmol), triethylamine (0.271 g, 2.682 mmol) and N,N-dimethylformamide (2 mL) were added to a flask under nitrogen protection. 2-amino-2,2-d$_2$-acetonitrile hydrochloride (0.124 g, 1.341 mmol) was added under stirring, and reacted for 20 h under room temperature. Purified water (2 mL) and saturated bicarbonate solution (2 mL) were added to the reaction mixture, and there was yellow solid precipitated. After stirred for 30 mins, it was filtered and washed by clear water. The crude product was obtained after drying, and was separated and purified by preparative chromatography to obtain yellow solid desired product (0.112 g, HPLC purity: 98.9%, yield: 60%). MS Calcd.: 420. MS Found: 421 (M+H)$^+$. 1H NMR (400 MHz, DMSO-d$_6$) δ 9.56 (1H, s), 9.35 (1H, s), 8.57-8.56 (1H, d), 8.29-8.27 (2H, d), 8.05-8.03 (2H, d), 7.70-7.68 (2H, d), 7.44-7.42 (1H, d), 6.99 (2H, s), 3.76 ppm (4H, s)

Example 5

The preparation of N-(cyanomethyl)-4-(2-(4-(2',2', 6',6'-d$_4$-morpholino)phenylamino)pyrimidin-4-yl) benzamide (compound 25)

4-(2-(4-(2',2',6',6'-d$_4$-morpholino)phenylamino)pyrimidin-4-yl)benzoic acid (0.170 g, 0.447 mmol), 1-ethyl-(3-dimethylaminopropyl) carbodiimide hydrochloride (0.103 g, 0.536 mmol), 1-hydroxy-phenylpropyl triazole (0.724 g, 0.536 mmol), triethylamine (0.271 g, 2.682 mmol) and N,N-dimethylformamide (2 mL) were added to a flask under nitrogen protection. 2-amino-acetonitrile hydrochloride (0.124 g, 1.341 mmol) was added under stirring, and reacted for 20 h under room temperature. Purified water (2 mL) and saturated bicarbonate solution (2 mL) were added to the reaction mixture, and there was yellow solid precipitated. After stirred for 30 mins, it was filtered and washed by clear water. The crude product was obtained after drying, and was separated by separation and purification of preparative chromatography to obtain yellow solid desired product (0.105 g, HPLC purity: 98.1%, yield: 56%); MS Calcd.: 418; MS Found: 419 (M+H)+; $^1$H NMR (400 MHz, DMSO-d$_6$) δ 9.65 (1H, s), 9.38-9.36 (1H, m), 8.58-8.56 (1H, d), 8.29-8.27 (2H, d), 8.05-8.03 (2H, d), 7.75-7.73 (2H, d), 7.46-7.45 (1H, d), 7.09 (2H, s), 4.37-4.36 (2H, d), 3.79 ppm (4H, s).

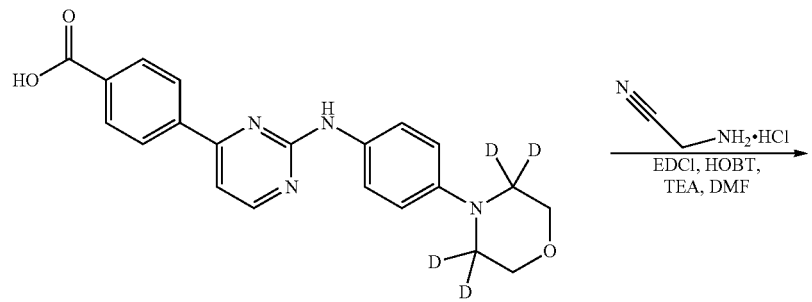

23

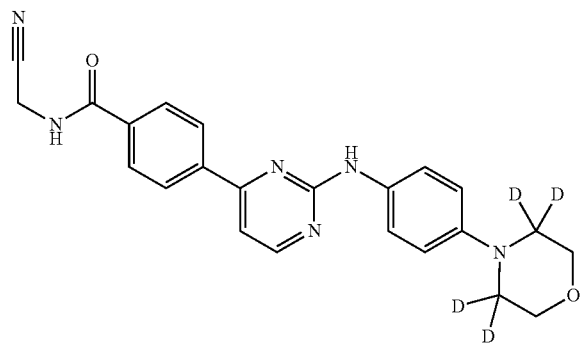

25

Example 6

The preparation of N-(cyano(d₂-methyl))-4-(2-(4-(3',3',5',5'-d₄-morpholinophenylamino)pyrimidin-4-yl)benzamide (compound 34)

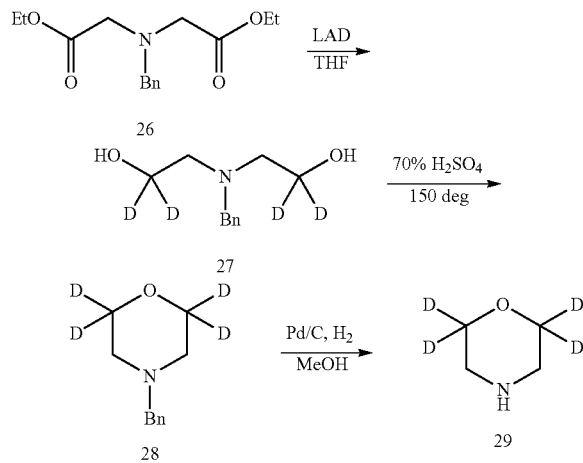

1. The preparation of 3,3,5,5-d₄-morpholine (compound 29)

1). The preparation of 2, 2'-(benzylimino)bis(1,1-d₂-ethanol) (compound 27)

Benzyl iminodiacetic acid diethyl ester (3.5 g, 12.53 mmol) and anhydrous tetrahydrofuran (35 mL) were added to the flask under the protection of nitrogen, deuterated lithium aluminum hydride (1.49 g, 35.5 mmol, purchased from J&K) was added in portionwise, and the inner temperature was kept under 10° C. It was heated to room temperature and stirred to react overnight. The reaction was monitored by HPLC. After the reaction was qualified, 7 mL of water and 3.5 mL of 15% aqueous sodium hydroxide were added to the reaction mixture under ice bath, and stirred for 30 min, then filtered and washed with tetrahydrofuran (20 mL). The filterate was concentrated to obtain yellow oily desired product (2.4 g, HPLC purity: 100%, yield: 96%); 1H NMR (400 MHz, CDCl₃) δ 7.37-7.27 (5H, m), 3.72 (2H, s), 2.75 (2H, s), 2.72 ppm (4H, s).

2). The preparation of N-benzyl-3,3,5,5-d₄-morpholine (compound 28)

2,2'-(benzylimino)bis(1,1-d₂-ethanol) (1.49 g, 35.5 mmol) and concentrated sulfuric acid (70%, 2 mL) were added to a flask. It was heated to 150° C. to react for 16 h. The reaction was monitored by HPLC. After the reaction was qualified, the reaction mixture was cooled to room temperature, and was poured into 25 mL of ice water, and the pH was neutralized to about 9 by adding solid potassium carbonate, and dichloromethane (2 mL) was added and stirred for 30 mins. After filteration, the filterate was extracted by dichloromethane for three times, the organic phase was dried on anhydrous sodium sulfate, and concentrated to obtain the yellow oily desired product (1.4 g, HPLC purity: 98.9%, yield 64%). ¹H NMR (400 MHz, CDCl₃) δ 7.36-7.28 (5H, m), 3.53 (2H, s), 2.46 ppm (4H, s).

3). The preparation of 3,3,5,5-d₄-morpholine (compound 29)

N-benzyl-3,3,5,5-d₄-morpholine (1.40 g, 7.72 mmol), palladium hydroxide (0.28 g, 20%) and methanol (14 mL) were added into the flask under hydrogen atmosphere, heated to 40° C., and reacted for 18 h. The reaction mixture was cooled to room temperature and filtered. The filterate was concentrated to obtain the yellow oily desired product (0.4 g, HPLC purity: 90%, yield 57%).

2. The preparation of N-(cyano(d₂-methyl))-4-(2-(4-(3',3',5',5'-d₄-morpholino)phenylamino)pyrimidin-4-yl)benzamide (compound 34)

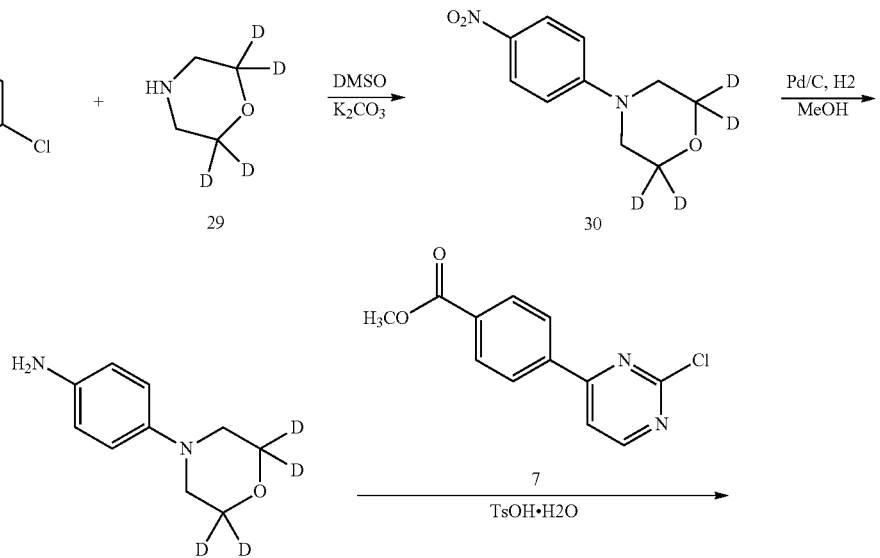

-continued

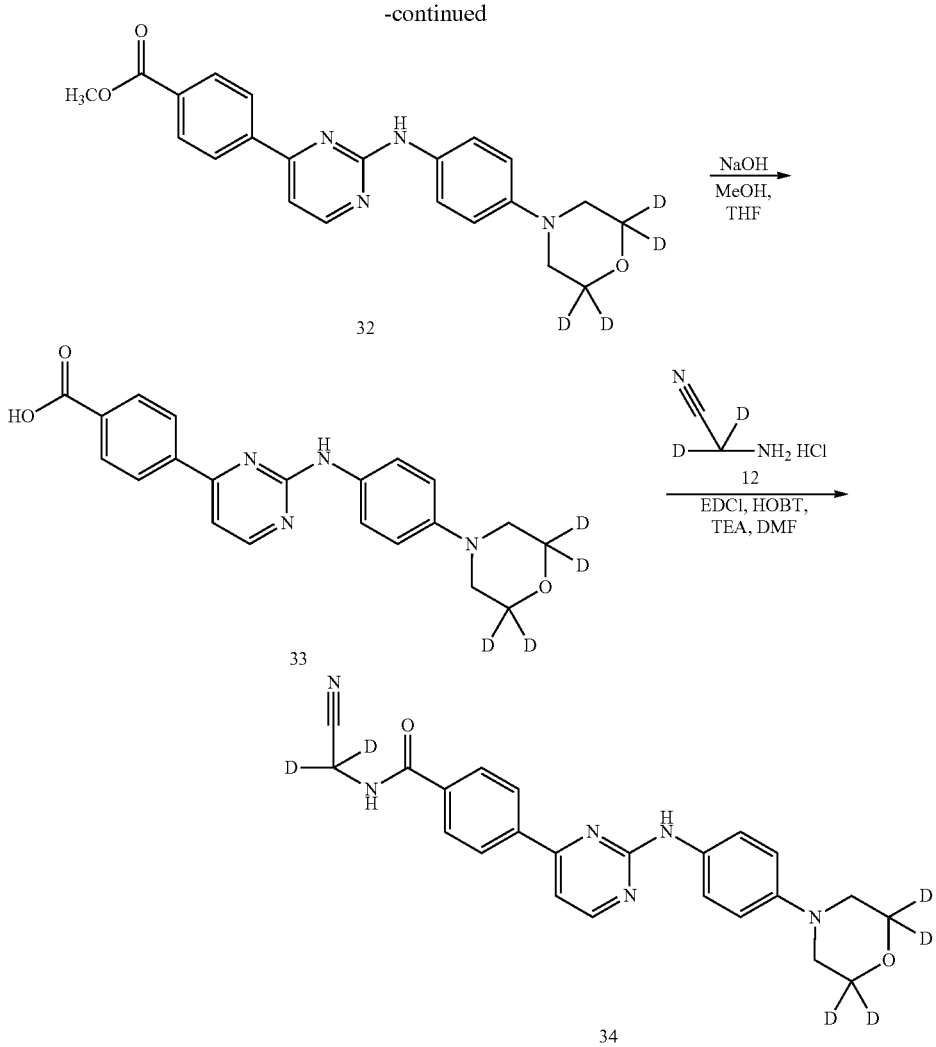

1). The preparation of 4-(4-nitrophenyl) (3',3',5',5'-$d_4$-morpholino) (compound 30)

4-chloronitrobenzene (1.210 g, 7.68 mmol), 3,3,5,5-$d_4$-morpholine (0.700 g, 7.68 mmol), potassium carbonate (3.18 g, 23.04 mmol) and dimethylsulfoxide (12 mL) were added to a flask, and heated to 100° C. and stirred for 18 h after that. The reaction was monitored by HPLC. After the reaction was qualified, the reaction mixture was cooled to room temperature, and was quenched by adding water (50 mL). There was yellow solid precipitated, filtered to obtain the crude product after stirred for 30 mins. The crude product was crystallized in the mixed solvent of ethyl acetate and petroleum ether (1/2.5, v/v, 15 mL) to obtain the solid desired product (0.500 g, HPLC purity: 96%, yield: 30%).

2). The preparation of 4-(3',3',5',5'-$d_4$-morpholino) phenylamine (compound 31)

4-(4-nitrophenyl) (3',3',5',5'-$d_4$-morpholino) (0.500 g, 2.356 mmol) and methanol (50 ml) were added to the hydrogenation reaction vessel. 10% Palladium on carbon (0.060 g) was added under nitrogen protection. The reaction system was replaced with hydrogen for 3-4 times, and was stirred under hydrogen pressure to react for 20 hours under 40° C. HPLC detected that the reaction has completed, and then the reaction solution was cooled to room temperature, and filtered through Celite. The residue was washed with methanol. The combined filtrate was concentrated under vacuum by rotary evaporator to give the crude product, and the crude product was isolated and purified by column chromatography to obtain solid desired product (0.170 g, HPLC purity: 95%, yield: 40%).

3). The preparation of 4-(2-(4-(3',3',5',5'-$d_4$-morpholino)phenylamino)pyrimidin-4-yl)methyl benzoate (compound 32)

4-(2-chloropyrimidin-4-yl)methyl benzoate (0.255 g, 1.026 mmol), 4-(3',3',5',5'-$d_4$-morpholino)phenylamine (0.170 g, 0.933 mmol) and 1,4-dioxane (14 mL) were added to a flask. P-toluenesulfonic acid monohydrate (0.195 g, 1.026 mmol) was added into the suspension under stirring. The reaction was heated to reflux for 20 h, and was detected by HPLC. After the reaction was qualified, the reaction mixture was concentrated under vacuum by rotary evaporator. Ethyl acetate (5 mL) and 5% aqueous sodium bicarbonate (5 mL) were added, yellow solid was precipitated, after stirred for 30 min, filtered to give the crude product.

The crude product was suspended in methanol (5 mL), pulped for 5 min, and filtered. The residue was washed with methanol, dried under vacuum to obtain solid desired product (0.200 g, HPLC purity: 92%, yield: 55%).

4), 4-(2-(4-(3',3',5',5'-d₄-morpholino)phenylamino)pyrimidin-4-yl)benzoate (compound 33)

4-(2-(4-(3',3',5',5'-d₄-morpholino)phenylamino)pyrimidin-4-yl)methyl benzoate (0.200 g, 0.507 mmol), sodium hydroxide (0.041 g, 1.014 mmol), water (1 ml), the mixed solvent of methanol and tetrahydrofuran (4 mL, 3:1) were added to the flask, heated to 65° C., and reacted for 2 h. The reaction mixture was cooled to room temperature, the solvent was removed, and the pH was adjusted to 3 by 10% diluted hydrochloric acid, filtered and dried to obtain grey solid. The crude product was grinded to powder. Methanol (2 mL) was added and pulped for 5 min, and then filtered and dried to obtain solid desired product (0.200 g, yield: 86%).

5). The preparation of N-(cyano(d₂-methyl)-4-(2-(4-(3',3',5',5'-d₄-morpholino)phenylamino)pyrimidin-4-yl)benzamide (compound 34)

4-(2-(4-(3',3',5',5'-d₄-morpholino)phenylamino)pyrimidin-4-yl)benzoic acid (0.100 g, 0.263 mmol), 1-ethyl-(3-dimethylaminopropyl) carbodiimide hydrochloride (0.061 g, 0.316 mmol), 1-hydroxy-phenylpropyl triazole (0.043 g, 0.316 mmol), triethylamine (0.159 g, 1.578 mmol) and N,N-dimethylformamide (2 mL) were added to a flask under nitrogen protection. 2-amino-2,2-d₂-acetonitrile hydrochloride (0.073 g, 0.789 mmol) was added under stirring, and reacted for 20 h under room temperature. Purified water (2 mL) and saturated bicarbonate solution (2 mL) were added to the reaction mixture, and there was yellow solid precipitated. After stirred for 30 mins, it was filtered and washed by clear water. The crude product was obtained after drying, and was separated and purified by preparative chromatography to obtain yellow solid desired product (0.050 g, HPLC purity: 98.9%, yield: 45%). MS Calcd.: 420. MS Found: 421 (M+H)⁺. ¹H NMR (400 MHz, DMSO-d₆) δ 9.57 (1H, s), 9.35 (1H, s), 8.56-8.55 (1H, d), 8.29-8.27 (2H, d), 8.04-8.02 (2H, d), 7.70-7.68 (2H, d), 7.44-7.42 (1H, d), 6.99-6.98 (2H, d), 3.08 ppm (4H, s).

Example 7

The preparation of N-(cyanomethyl)-4-(2-(4-(3',3',5',5'-d₄-morpholino)phenylamino)pyrimidin-4-yl)benzamide (compound 35)

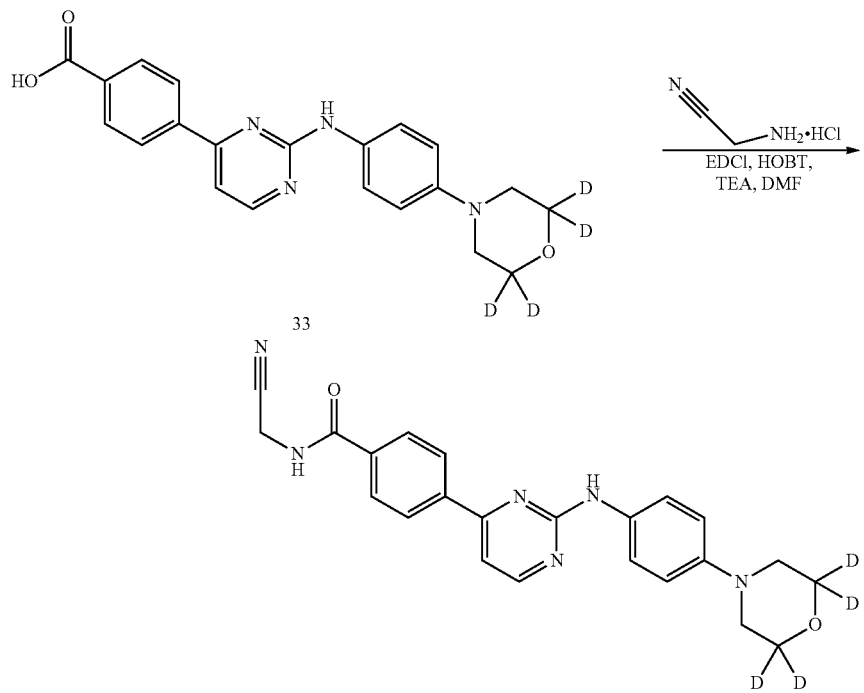

4-(2-(4-(3',3',5',5'-d4-morpholino)phenylamino)pyrimidin-4-yl)benzoic acid (0.100 g, 0.263 mmol), 1-ethyl-(3-dimethylaminopropyl) carbodiimide hydrochloride (0.061 g, 0.316 mmol), 1-hydroxy-phenylpropyl triazole (0.043 g, 0.316 mmol), triethylamine (0.159 g, 1.578 mmol) and N,N-dimethylformamide (2 mL) were added to a flask under nitrogen protection. 2-amino-acetonitrile hydrochloride (0.073 g, 0.789 mmol) was added under stirring, and reacted for 20 h under room temperature. Purified water (2 mL) and saturated bicarbonate solution (2 mL) were added to the reaction mixture, and there was yellow solid precipitated. After stirred for 30 mins, it was filtered and washed by clear water. The crude product was obtained after drying, and was separated and purified by preparative chromatography to obtain yellow solid desired product (0.060 g, HPLC purity: 98.4%, yield: 55%); MS Calcd.: 418; MS Found: 419 (M+H)⁺. 1H NMR (400 MHz, DMSO-d₆) δ 9.62 (1H, s), 9.38-9.35 (1H, m), 8.57-8.56 (1H, d), 8.29-8.27 (2H, d), 8.04-8.02 (2H, d), 7.73-7.70 (2H, d), 7.45-7.44 (1H, d), 7.05 (2H, s), 4.37-4.36 (2H, d), 3.14 ppm (4H, s).

Example 8
The preparation of N-(cyano(d₂-methyl))-4-(2-(4-morpholinophenylamino)pyrimidin-4-yl)benzamide (compound 41)
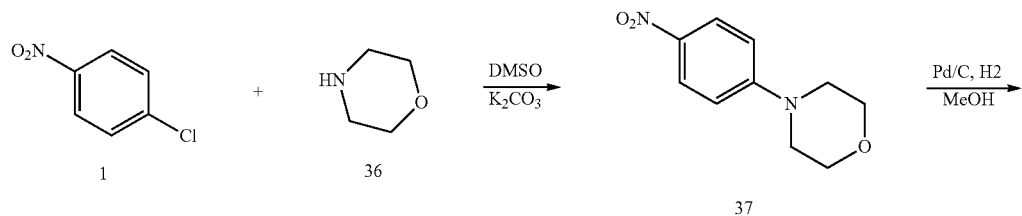
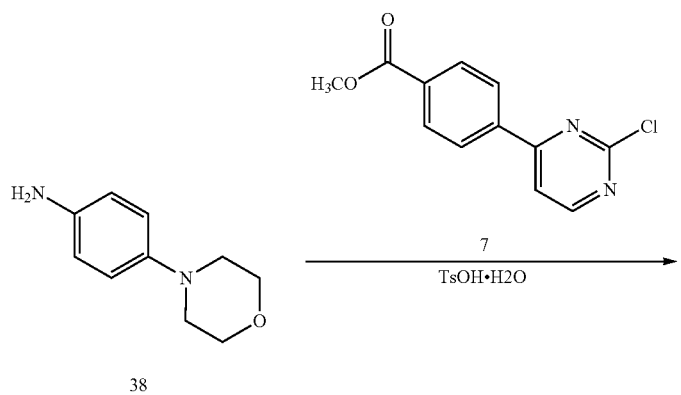
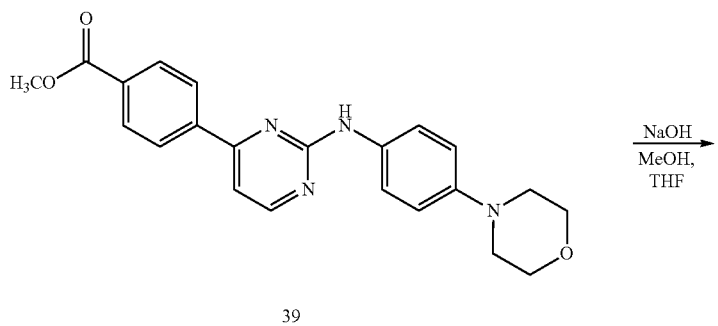
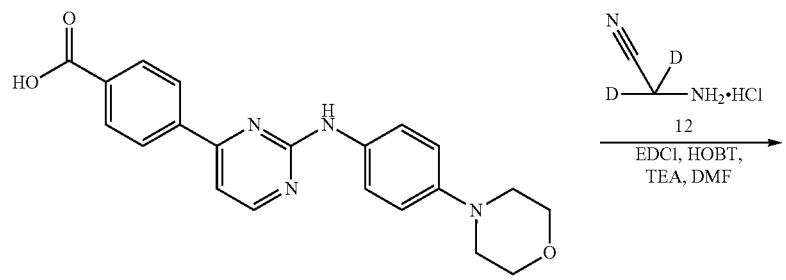

-continued

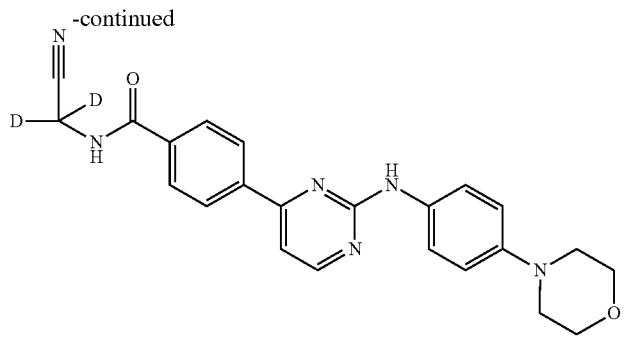

41

1. The preparation of 4-(4-nitrophenyl)(morpholine) (compound 37)

4-chloronitrobenzene (1.00 g, 6.35 mmol), morpholine (0.608 g, 7.68 mmol), potassium carbonate (1.76 g, 12.7 mmol), dimethylsulfoxide (11 mL) were added to a flask. After that, it was heated to 100° C. and stirred for 18 h. The reaction was monitored by HPLC. After the reaction was qualified, the reaction mixture was cooled to room temperature, and was quenched by adding water (50 mL). There was yellow solid precipitated, filtered to obtain the crude product after stirred for 30 mins. The crude product was crystallized in the mixed solvent of ethyl acetate and petroleum ether (1/2.5, v/v, 16 mL) to obtain yellow solid desired product (0.800 g, HPLC purity: 98.9%, yield 60%). $^1$H NMR (400 MHz, CDCl$_3$) δ 8.18-8.15 (2H, d), 6.87-6.84 (2H, d), 3.90-3.88 (4H, t), 3.41-3.38 ppm (4H, t).

2. The preparation of 4-(morpholino)phenylamine (compound 38)

4-(4-nitrophenyl) morpholine (0.600 g, 2.882 mmol) and methanol (60 ml) were added to the hydrogenation reaction vessel. 10% Palladium on carbon (0.060 g) was added under nitrogen protection. The reaction system was replaced with hydrogen for 3-4 times, and was stirred under hydrogen pressure to react for 18 hours under 40° C. HPLC detected that the reaction has completed, and then the reaction solution was cooled to room temperature, and filtered through Celite. The residue was washed with methanol. The combined filtrate was concentrated under vacuum by rotary evaporator to give the solid desired product (0.500 g, HPLC purity: 97.1%, yield: 97%). $^1$H NMR (400 MHz, DMSO-d$_6$) δ 6.83-6.80 (2H, d), 6.71-6.68 (2H, d), 3.88-3.86 (4H, t), 3.46 (2H, s), 3.06-3.03 ppm (4H, t).

3. The preparation of 4-(2-((4-morpholino)phenylamino)pyrimidin-4-yl)methyl benzoate (compound 39)

4-(2-chloropyrimidin-4-yl)methyl benzoate (0.651 g, 2.617 mmol), 4-(morpholino)phenylamine (0.513 g, 2.878 mmol) and 1,4-dioxane (16 mL) were added to a flask. P-toluenesulfonic acid monohydrate (0.547 g, 2.878 mmol) was added to the suspension under stirring. After heated to reflux for 20 h, the reaction was detected by HPLC. After the reaction was qualified, the reaction mixture was cooled to 30° C., and concentrated under vacuum by rotary evaporator. Ethyl acetate (5 mL) and 5% aqueous sodium bicarbonate (5 mL) were added, yellow solid was precipitated, after stirred for 30 min, filtered to give the crude product. The crude product was suspended in methanol (8 mL), pulped for 5 min, and filtered. The residue was washed with methanol, dried under vacuum to obtain solid desired product (0.860 g, HPLC purity: 97.6%, yield: 84%); $^1$H NMR (400 MHz, CDCl$_3$) δ 8.50-8.49 (1H, d), 8.17-8.13 (4H, m), 7.60-7.58 (2H, d), 7.17-7.16 (2H, d), 6.99-6.97 (2H, d), 3.98 (3H, s), 3.92-3.89 (4H, t), 3.18-3.15 ppm (4H, t).

4, 4-(2-(4-(morpholino)phenylamino)pyrimidin-4-yl)benzoic acid (compound 40)

4-(2-(4-(morpholino)phenylamino)pyrimidin-4-yl) methyl benzoate (0.860 g, 2.203 mmol), sodium hydroxide (0.176 g, 4.405 mmol), water (3.5 ml), the mixed solvent of methanol and tetrahydrofuran (12 mL, 3:1) were added to the flask, heated to 65° C., and reacted for 2 h. The reaction mixture was cooled to room temperature, the solvent was removed, and the pH was adjusted to 3 by 10% diluted hydrochloric acid, filtered and dried to obtain grey solid. The crude product was grinded to powder. Methanol (10 mL) was added and pulped for 5 min, and then filtered and dried to obtain solid desired product (0.730 g, HPLC purity: 97.7%, yield: 88%).

5. The preparation of N-(cyano(d$_2$-methyl))-4-(2-(4-(morpholino)phenylamino)pyrimidin-4-yl)benzamide (compound 41)

4-(2-(4-(morpholino)phenylamino)pyrimidin-4-yl)benzoic acid (0.230 g, 0.611 mmol), 1-ethyl-(3-dimethylaminopropyl) carbodiimide hydrochloride (0.141 g, 0.733 mmol), 1-hydroxy-phenylpropyl triazole (0.099 g, 0.733 mmol), triethylamine (0.371 g, 3.666 mmol) and N,N-dimethylformamide (2.5 mL) were added to a flask under nitrogen protection. 2-amino-2,2-d$_2$-acetonitrile hydrochloride (0.173 g, 1.833 mmol) was added under stirring, and reacted for 20 h under room temperature. Purified water (3 mL) and saturated bicarbonate solution (3 mL) were added to the reaction mixture, and there was yellow solid precipitated. After stirred for 30 mins, it was filtered and washed by clear water. The crude product was obtained after drying, and was separated and purified by preparative chromatography to obtain yellow solid desired product (0.183 g, HPLC purity: 99%, yield: 72%); MS Calcd.: 416. MS Found: 417 (M+H)+; $^1$H NMR (400 MHz, DMSO-d$_6$) δ 9.65 (1H, s), 9.35 (1H, s), 8.57-8.56 (1H, d), 8.29-8.27 (2H, d), 8.05-8.03 (2H, d), 7.75-7.73 (2H, d), 7.46-7.45 (1H, d), 7.09-7.07 (2H, d), 3.79-4.36 (4H, t), 3.17 ppm (4H, s).

Example 9

The preparation of N-(cyanomethyl)-4-(2-(4-morpholinophenylamino)pyrimidin-4-yl)benzamide (compound 42, control compound)

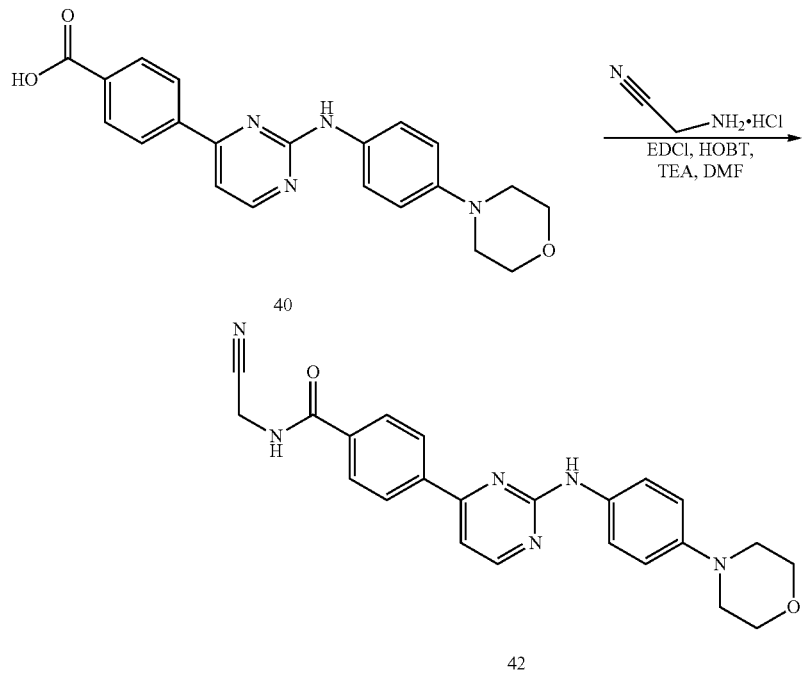

4-(2-(4-(morpholino)phenylamino)pyrimidin-4-yl)benzoic acid (0.500 g, 1.328 mmol), 1-ethyl-(3-dimethylaminopropyl) carbodiimide hydrochloride (0.305 g, 1.594 mmol), 1-hydroxy-phenylpropyl triazole (0.215 g, 1.594 mmol), triethylamine (0.805 g, 7.968 mmol) and N,N-dimethylformamide (5 mL) were added to a flask under nitrogen protection. 2-amino-acetonitrile hydrochloride (0.368 g, 3.985 mmol) was added under stirring, and reacted for 20 h under room temperature. Purified water (5 mL) and saturated bicarbonate solution (5 mL) were added to the reaction mixture, and there was yellow solid precipitated. After stirred for 30 mins, it was filtered and washed by clear water. The crude product was obtained after drying, and was separated and purified by preparative chromatography to obtain yellow solid desired product (0.130 g, PLC purity: 98.3%, yield: 24%); MS Calcd.: 414; MS Found: 415 (M+H)+; $^1$H NMR (400 MHz, DMSO-$d_6$) δ 9.63 (1H, s), 9.38-9.35 (1H, m), 8.57-8.56 (1H, d), 8.29-8.27 (2H, d), 8.05-8.03 (2H, d), 7.74-7.71 (2H, d), 7.46-7.44 (1H, d), 7.07-7.05 (2H, d), 4.37-4.36 (2H, d), 3.80-3.78 (4H, t), 3.15 ppm (4H, s).

Example 10

Pharmacokinetic Evaluation in Rats 12 male Sprague-Dawley rats, 7-8 weeks old, of approximately 200 g body weight, were divided into three groups, four in each group. A dose of 3 mg/kg of (a) the control compound prepared in example 9: N-(cyanomethyl)-4-(2-(4-morpholinophenyl amino)pyrimidin-4-yl)benzamide and (b) compound of the present invention: compounds prepared in example 1-8 is joint oral garvage administrated each time, and the pharmacokinetic difference thereof was assessed.

Rats were feed with standard feed, and were given water, and were started to fast 16 hours before the test. The drug was dissolved in PEG400 and dimethylsulfoxide. Orbital blood collection was conducted, and the blood collection time is 0.25 hour, 0.5 hour, 1 hour, 2 hour, 4 hour, 6 hour, 8 hour, 12 hour, 24 hour, 36 hour and 48 hour after administration.

After inhalation of ether, the rats were shortly anesthesiaed; 300 μL of blood were collected from orbit into a test tube. There were 30 μL of 1% heparin saline solutions in the test tube. Before use, test tubes were dried overnight at 60° C. After the blood sample was collected in the subsequent time point, rats were anesthetized with ether and sacrificed.

After blood sampling, the tube was gently inverted at least 5 times immediately to ensure adequate mixing, and was placed on ice. Blood samples were 5000 rpm centrifuged at 4° C. for 5 minutes to separate the plasma and red blood cells. 100 μL of plasma was pipetted into a clean plastic centrifuge tube, and the name of compounds and the time point were indicated. Plasma was stored in −80° C. before use for the analysis. The concentration of the compound of the invention in plasma was determined with LC-MS/MS. The pharmacokinetic parameters were calculated based on the blood drug concentration of each animal at different time points. It can be seen from the results that, when compared to the example 9 control compound, compounds of the present invention (example 1-8 compounds) are of better pharmacokinetics in animals (see Table 1-3), and thereby having better pharmacodynamic and treatment effect.

TABLE 1

The pharmacokinetic parameters in rats after administered 3 mg/kg by gavage

| Group | Compounds | Number of rats | Tmax (h) | Cmax (ng/ml) | AUClast (h*ng/ml) | AUCINF_obs (h*ng/ml) |
|---|---|---|---|---|---|---|
| G1 | example 9 | 1 | 0.25 | 368 | 2288 | 2297 |
| | | 2 | 4 | 79.4 | 443 | 480 |
| | | 3 | 4 | 354 | 2445 | 2508 |
| | | 4 | 2 | 180 | 1317 | 1326 |
| | | Mean | 2.56 | 245 | 1623 | 1653 |
| | | SD | 1.81 | 140 | 932 | 936 |
| | example 8 | 1 | 0.25 | 469 | 3092 | 3105 |
| | | 2 | 4 | 101 | 574 | 616 |
| | | 3 | 4 | 438 | 3046 | 3129 |
| | | 4 | 2 | 227 | 1632 | 1642 |
| | | Mean | 2.56 | 309 | 2086 | 2123 |
| | | SD | 1.81 | 175 | 1215 | 1222 |
| | example 6 | 1 | 0.25 | 423 | 2726 | 2739 |
| | | 2 | 4 | 94.6 | 514 | 561 |
| | | 3 | 4 | 403 | 2841 | 2922 |
| | | 4 | 2 | 207 | 1519 | 1529 |
| | | Mean | 2.56 | 282 | 1900 | 1938 |
| | | SD | 1.81 | 158 | 1101 | 1106 |

The result shows that the Cmax of example 8 compound (309±175 ng/mL) is significantly higher than that of example 9 control compound (245±140 ng/mL); the AUClast of example 8 compound (2086±1215 ng·h/mL) is significantly higher than that of example 9 control compound (1623±932 ng-h/mL).

The Cmax of example 6 compound (282±158 ng/mL) is significantly higher than that of example 9 control compound (245±140 ng/mL); the AUClast of example 6 compound (1900±1101 ng·h/mL) is significantly higher than that of example 9 control compound (1623±932 ng·h/mL).

TABLE 2

The pharmacokinetic parameters in rats after administered 3 mg/kg by gavage

| Group | Compounds | Number of rats | Tmax (h) | Cmax (ng/ml) | AUClast (h*ng/ml) | AUCINF_obs (h*ng/ml) |
|---|---|---|---|---|---|---|
| G2 | example 9 | 5 | 2 | 858 | 4081 | 4106 |
| | | 6 | 4 | 567 | 3323 | 3340 |
| | | 7 | 4 | 514 | 3177 | 3207 |
| | | 8 | 4 | 415 | 2266 | 2301 |
| | | Mean | 3.5 | 589 | 3212 | 3238 |
| | | SD | 1 | 190 | 744 | 740 |
| | example 5 | 5 | 2 | 1410 | 6816 | 6848 |
| | | 6 | 4 | 922 | 5455 | 5492 |
| | | 7 | 4 | 875 | 5473 | 5524 |
| | | 8 | 4 | 686 | 3813 | 3897 |
| | | Mean | 3.5 | 972 | 5389 | 5440 |
| | | SD | 1 | 307 | 1229 | 1207 |

The result shows that the Cmax of example 5 compound (972±307 ng/mL) is significantly higher than that of example 9 control compound (589±190 ng/mL); the AUClast of example 5 compound (5389±1229 ng·h/mL) is significantly higher than that of example 9 control compound (3212±744 ng·h/mL).

TABLE 3

The pharmacokinetic parameters in rats after administered 3 mg/kg by gavage

| Group | Compounds | Number of rats | Tmax (h) | Cmax (ng/ml) | AUClast (h*ng/ml) | AUCINF_obs (h*ng/ml) |
|---|---|---|---|---|---|---|
| G3 | example 9 | 9 | 4 | 579 | 3415 | 3475 |
| | | 10 | 4 | 336 | 1803 | 1847 |
| | | 11 | 2 | 276 | 1752 | 1797 |
| | | 12 | 4 | 270 | 1807 | 1845 |
| | | Mean | 3.5 | 365 | 2194 | 2241 |
| | | SD | 1 | 146 | 814 | 823 |
| | example 1 | 9 | 4 | 1060 | 6168 | 6305 |
| | | 10 | 4 | 596 | 3251 | 3367 |
| | | 11 | 2 | 476 | 3157 | 3254 |
| | | 12 | 4 | 483 | 3244 | 3323 |
| | | Mean | 3.5 | 653 | 3955 | 4062 |
| | | SD | 1 | 275 | 1476 | 1496 |
| | example 3 | 9 | 4 | 694 | 4101 | 4180 |
| | | 10 | 4 | 419 | 2299 | 2354 |
| | | 11 | 2 | 329 | 2193 | 2265 |
| | | 12 | 4 | 344 | 2287 | 2346 |
| | | Mean | 3.5 | 447 | 2720 | 2786 |
| | | SD | 1 | 170 | 922 | 930 |

The result shows that the Cmax of example 1 compound (653±275 ng/mL) is significantly higher than that of example 9 control compound (365±146 ng/mL); the AUClast of example 8 compound (3955±1476 ng·h/mL) is significantly higher than that of example 9 control compound (2194±814 ng·h/mL).

The Cmax of example 3 compound (447±170 ng/mL) is significantly higher than that of example 9 control compound (365±146 ng/mL); the AUClast of example 3 compound (2720±922 ng-h/mL) is significantly higher than that of example 9 control compound (2194±814 ng·h/mL).

Example 11

The In Vitro Pharmacodynamics of the Compounds of the Invention for JAK Kinases

The Determination of the Inhibiting Effect $IC_{50}$ on Kinases JAK1 and JAK2

The JAK kinase inhibitory activity test was conducted in the 96-well plates. The compounds to be tested (any one of the compounds prepared in Example 1-7) were dissolved in DMSO, and was prepared into test liquid of different concentrations. They were incubated with JAK1 or JAK2 tyrosine kinase in phosphotyrosine assay buffer (5 mM HEPES, pH 7.5, 50 mM $MgCl_2$, 50 mM NaCl, 100 mM sodium vanadate and 0.1% Tween 20) for 20 minutes. The substrate (e.g.: biotin-EGPWLEEEEEAYGWMDF-$NH_2$ or biotin-EQEDEPEGDYFEWLEPE) was added, and incubated for 60 min. Each reaction well was added streptavidin donor beads under light illumination, and were incubated for 150 minutes. The plate was read out after washing, and $IC_{50}$ values were calculated from these data.

The results are shown in Table 4. It can be seen that the compounds of the present invention are of excellent inhibitory activity to both JAK1 and JAK2 kinases.

TABLE 4

| Compounds | JAK1 kinase inhibitory activity ($IC_{50}$) | JAK2 kinase inhibitory activity ($IC_{50}$) |
|---|---|---|
| example 1 | <20 nM | <20 nM |
| example 3 | <20 nM | <20 nM |

TABLE 4-continued

| Compounds | JAK1 kinase inhibitory activity (IC$_{50}$) | JAK2 kinase inhibitory activity (IC$_{50}$) |
|---|---|---|
| example 4 | <20 nM | <20 nM |
| example 5 | <20 nM | <20 nM |
| example 6 | <20 nM | <20 nM |
| example 7 | <20 nM | <20 nM |
| example 8 | <20 nM | <20 nM |
| example 9 (control compound) | <20 nM | <20 nM |

Example 12

The In Vitro Pharmacodynamic Evaluation of Compounds of the Present Invention to Inhibit STAT Phosphorylation Activity Reagents:
DMEM culture medium, purchased from Mediatech Company
Anti-phospho STAT3 antibody, purchased from Cell Signaling Technology Company
Anti-actin antibody, purchased from Sigma Company
Experimental Method:
HCT116 cells (from ATCC) was cultured in DMEM culture medium comprising 10% fetal bovine serum, 2 mM glutamine, 100 U/ml Penicillin and 100 mg/ml streptomycin. The compounds were dissolved in DMSO. Compounds of different concentrations (0.6 µM, 1.2 µM) are added into the culture medium, and DMSO was used as negative control, and the compound of example 9 (0.6 µM, 1.2 µM) was used as positive control. The cells were treated for 2 hours, and then the proteins were harvested for Western Blotting analysis.
Experimental Results:
FIG. 1 shows that the compounds of the present invention have JAK-STAT signaling pathway inhibitory activity, and the STAT3 phosphorylation inhibitory activity is similar with or better than that of the example 9 control compound.

Example 13

Pharmaceutical Composition

| Compound (example 1-8) | 10 g |
|---|---|
| Starch | 140 g |
| Microcrystalline cellulose | 60 g |

The above materials were mixed by conventional methods and put into common gelatine capsules to obtain 1000 capsules.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method of treating inflammation or an immune disease in a subject in need thereof, the method comprising administering to the subject a pharmaceutical composition comprising an effective amount of a deuterated phenyl amino pyrimidine compound of formula (I), or a crystal form, pharmaceutically acceptable salt, hydrate or solvate thereof:

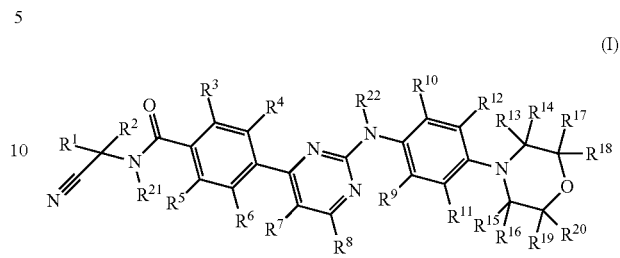

(I)

wherein
$R^1$, $R^2$, $R^{13}$, $R^{14}$, $R^{15}$, $R^{16}$, $R^{17}$, $R^{18}$, $R^{19}$, $R^{20}$, $R^{21}$ and $R^{22}$ are each independently hydrogen or deuterium;
$R^3$, $R^4$, $R^5$, $R^6$, $R^7$, $R^8$, $R^9$, $R^{10}$ and $R^{11}$ are each independently hydrogen, deuterium, halogen, undeuterated C1-C6 alkyl or C1-C6 alkoxy, mono- or multi-deuterated or fully deuterated C1-C6 alkyl or C1-C6 alkoxy, or mono- or multi-halogenated or fully halogenated C1-C6 alkyl or C1-C6 alkoxy;
$R^{12}$ is selected from the group consisting of hydrogen, deuterium, halogen, $OR^{23}$, $COOR^{23}$, $COSR^{23}$, $CONHR^{23}$ and $CON(R^{23})_2$; wherein $R^{23}$ is selected from the group consisting of hydrogen, deuterium, substituted or unsubstituted C1-C6 alkyl, and substituted or unsubstituted C3-C8 cycloalkyl, wherein the substituent is selected from the group consisting of halogen, cyano, C1-C6 alkyl and C1-C6 alkoxy;
with the proviso that at least one of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $R^{18}$, $R^{19}$, $R^{20}$, $R^{21}$ or $R^{22}$ is deuterated or deuterium.

2. The method of claim 1, wherein $R^1$ and R are $R^2$ are hydrogen or deuterium.

3. The method of claim 1, wherein $R^{12}$ is hydrogen or deuterium.

4. The method of claim 1, wherein $R^{13}$, $R^{14}$, $R^{15}$ and $R^{16}$ are hydrogen or deuterium.

5. The method of claim 1, wherein $R^{17}$, $R^{18}$, $R^{19}$ and $R^{20}$ are hydrogen or deuterium.

6. The method of claim 1, wherein $R^{13}$, $R^{14}$, $R^{15}$, $R^{16}$, $R^{17}$, $R^{18}$, $R^{19}$ and $R^{20}$ are deuterium.

7. The method of claim 1, wherein $R^3$, $R^4$, $R^5$, $R^6$, $R^7$ and $R^8$ are each independently selected from the group consisting of hydrogen, deuterium, mono- or multi-deuterated or fully deuterated methyl or methoxyl, and mono- or multi-deuterated or fully deuterated ethyl or ethoxyl.

8. The method of claim 1, wherein the compound is selected from the group consisting of

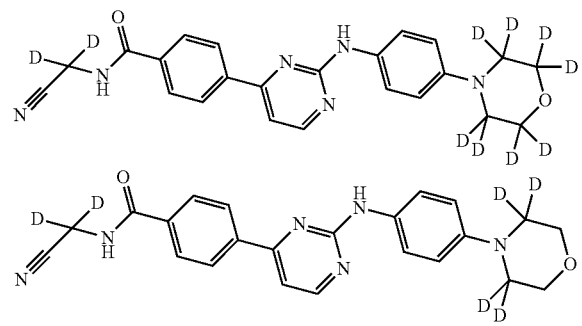

-continued

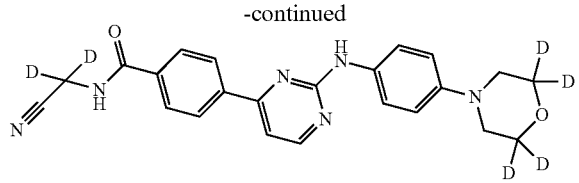

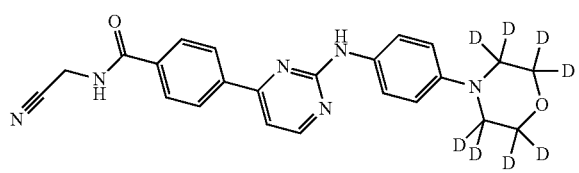

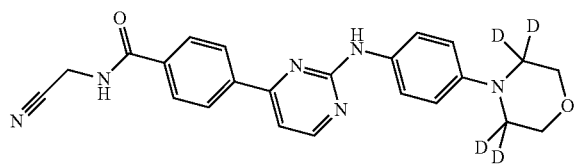

-continued

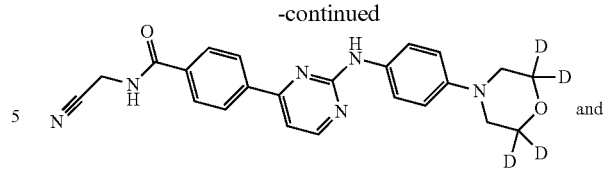

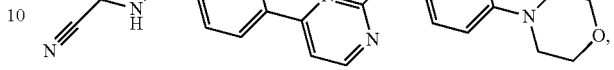

or a pharmaceutically acceptable salt thereof.

9. The method of claim 1, wherein the compound inhibits a protein kinase in the subject.

10. The method of claim 9, wherein the protein kinase is a JAK kinase.

11. The method of claim 1, wherein the inflammation or immune disease is selected from the group consisting of rheumatoid arthritis, osteoarthritis, rheumatoid spondylitis, gout, asthma, bronchitis, rhinitis, chronic obstructive pulmonary disease, and cystic fibrosis.

* * * * *